(12) United States Patent
Park et al.

(10) Patent No.: US 11,779,232 B2
(45) Date of Patent: *Oct. 10, 2023

(54) FLEXIBLE PRESSURE SENSOR USING MULTI-MATERIAL 3D-PRINTED MICROCHANNEL MOLD AND METHOD FOR MANUFACTURING THE SAME

(71) Applicant: KOREA ADVANCED INSTITUTE OF SCIENCE AND TECHNOLOGY, Daejeon (KR)

(72) Inventors: Inkyu Park, Daejeon (KR); Kyuyoung Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 285 days.

This patent is subject to a terminal disclaimer.

(21) Appl. No.: 17/016,851

(22) Filed: Sep. 10, 2020

(65) Prior Publication Data

US 2021/0137398 A1 May 13, 2021

Related U.S. Application Data

(63) Continuation-in-part of application No. 16/860,179, filed on Apr. 28, 2020, now Pat. No. 11,566,959.

(30) Foreign Application Priority Data

| Apr. 30, 2019 | (KR) | 10-2019-0050718 |
| Apr. 27, 2020 | (KR) | 10-2020-0050782 |
| May 29, 2020 | (KR) | 10-2020-0064878 |

(51) Int. Cl.
*A61B 5/024* (2006.01)
*A61B 5/021* (2006.01)
(Continued)

(52) U.S. Cl.
CPC ........ *A61B 5/02444* (2013.01); *A61B 5/0245* (2013.01); *A61B 5/02125* (2013.01);
(Continued)

(58) Field of Classification Search
CPC ............................ G01L 19/146; G01L 5/1623
(Continued)

(56) References Cited

U.S. PATENT DOCUMENTS 3,304,528 A * 2/1967 Rastrelli .................. G01L 1/20
338/114
9,228,822 B2 * 1/2016 Majidi ..................... G01B 7/18
(Continued)

FOREIGN PATENT DOCUMENTS

| JP | 2013156102 A | 8/2013 |
| KR | 20120054206 A | 5/2012 |
| KR | 10-2018-0102412 A | 9/2018 |

OTHER PUBLICATIONS

Kyuyoung Kim, "Materials-to-Devices for Integrated Wearable Systems—Energy Harvesting and Storage, Sensors/Actuators and Integration", Symposium BM08, Publication Nov. 28, 2018, Sheraton, 2nd Floor, Grand Ballroom.
(Continued)

*Primary Examiner* — Nathaniel T Woodward
(74) *Attorney, Agent, or Firm* — NIXON PEABODY LLP

(57) ABSTRACT

The present invention relates to a flexible pressure sensor using a multi-material 3D-printed microchannel mold, and a method for manufacturing the same, and more particularly, to a flexible pressure sensor having improved flexibility, sensitivity, and stability for use in a wearable device, and a method for manufacturing the same. Further, the present invention relates to a physical sensor for measuring a force applied from the outside, and more particularly, to a multi-directional physical sensor using a multi-layer microchannel (Continued)

array, which may sense all forces applied from the outside in three-dimensional directions such as a perpendicular direction and a parallel direction by applying the multi-layer microchannel array to a body having a three-dimensionally protruding shape.

17 Claims, 54 Drawing Sheets

(51) Int. Cl.
*A61B 5/0245* (2006.01)
*A61B 5/00* (2006.01)
*B33Y 10/00* (2015.01)
*G01L 1/22* (2006.01)
*A61B 5/282* (2021.01)

(52) U.S. Cl.
CPC .......... *A61B 5/02438* (2013.01); *A61B 5/447* (2013.01); *A61B 5/6804* (2013.01); *A61B 5/7278* (2013.01); *B33Y 10/00* (2014.12); *G01L 1/2287* (2013.01); *A61B 5/282* (2021.01); *A61B 2562/028* (2013.01); *A61B 2562/0247* (2013.01); *A61B 2562/04* (2013.01); *A61B 2562/12* (2013.01); *A61B 2562/164* (2013.01); *A61B 2562/168* (2013.01)

(58) Field of Classification Search
USPC .......................................................... 73/725
See application file for complete search history.

(56) References Cited

U.S. PATENT DOCUMENTS

| | | | |
|---|---|---|---|
| 9,797,791 B2* | 10/2017 | Vogt | G01L 1/02 |
| 9,841,331 B2* | 12/2017 | Wood | A61F 2/105 |
| 10,151,649 B2* | 12/2018 | Lewis | G01L 1/18 |
| 2003/0163055 A1* | 8/2003 | McLaughlin | A61B 5/0285 |
| | | | 600/504 |
| 2012/0118066 A1* | 5/2012 | Majidi | G01L 1/205 |
| | | | 73/719 |
| 2019/0242690 A1* | 8/2019 | Hu | B81B 3/0097 |

OTHER PUBLICATIONS

Kyuyoung Kim, "Highly Sensitive and Robust Soft Pressure Sensor using 3D-structured Microchannel and Liquid Metal for Health Monitoring Applications", 2018 MRS Fall Meeting, Nov. 28, 2018, Boston, Massachusetts.

Korean Office Action for Application No. 10-2020-0064878, dated Jul. 14, 2021.

* cited by examiner

Ref.

115
120

Model#1

Model#2
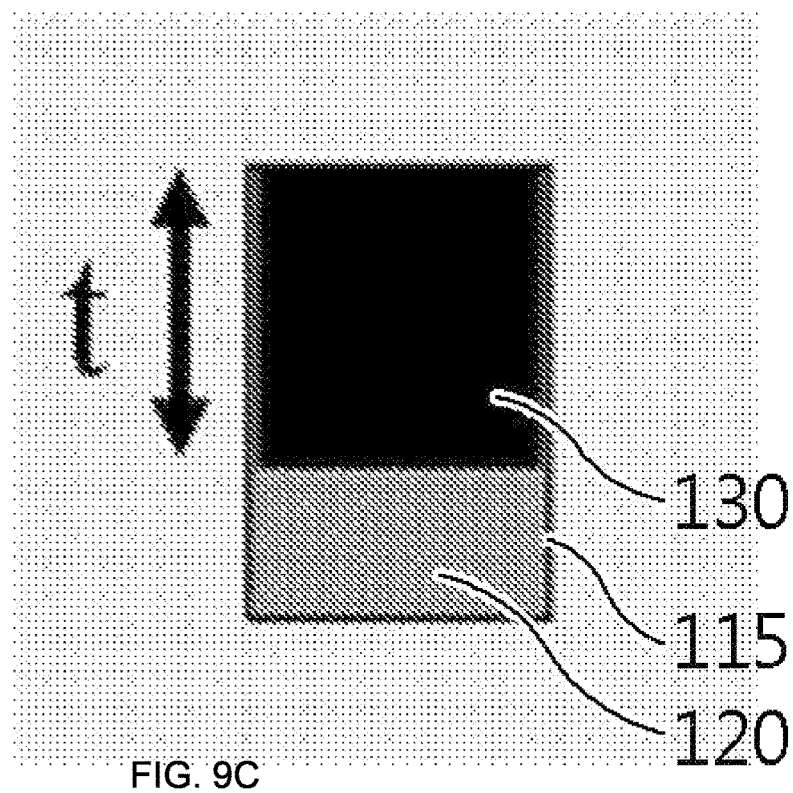
FIG. 9C
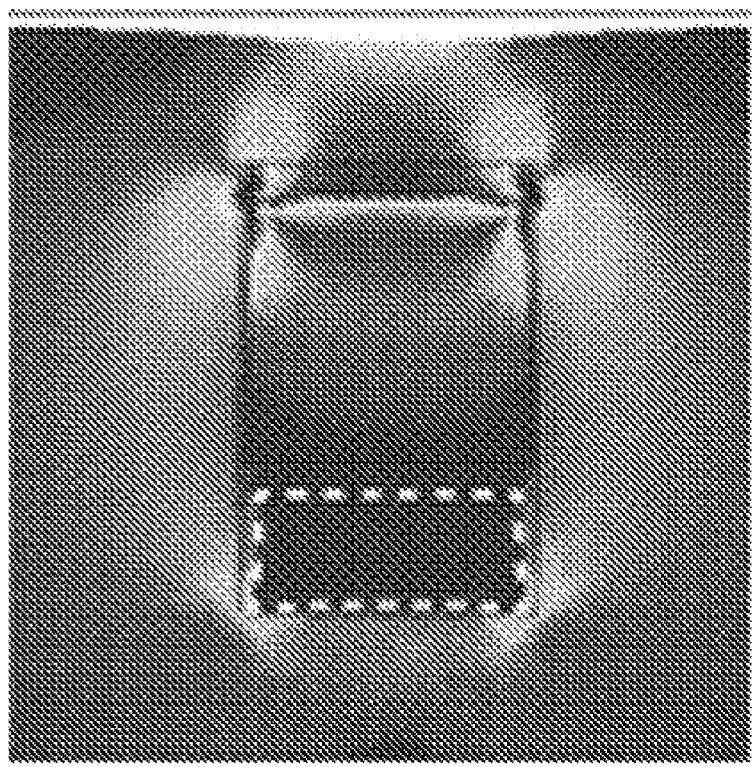

|  | Ref (t=0) | Model#1 (t=200) | Model#2 (t=400) |
|---|---|---|---|
| $\Delta A$ ($= A'-A$) | -5.37 | -8.06 | -11.1 |
| ratio | 1 | 1.5 | 2.07 |

FLEXIBLE PRESSURE SENSOR USING MULTI-MATERIAL 3D-PRINTED MICROCHANNEL MOLD AND METHOD FOR MANUFACTURING THE SAME

CROSS-REFERENCE TO RELATED APPLICATIONS

This application is a continuation-in-part ("CIP") of applicant's earlier application U.S. Ser. No. 16/860,179, filed Apr. 28, 2020, titled "SOFT PRESSURE SENSOR USING MULTI-MATERIAL 3D-PRINTED MICROCHANNEL MOLDS AND METHOD FOR MAKING THE SENSOR", which in turn, claims priority under U.S.C. § 119 to Korean Patent Application No. 10-2019-0050718 filed on Apr. 30, 2019, Korean Patent Application No. 10-2020-0050782 filed on Apr. 27, 2020 and Korean Patent Application No. 10-2020-0064878 filed on May 29, 2020, in the Korean Intellectual Property Office, the disclosures of which are incorporated herein by reference in their entirety.

TECHNICAL FIELD

The following disclosure relates to a flexible pressure sensor using a multi-material 3D-printed microchannel mold, and a method for manufacturing the same, and more particularly, to a flexible pressure sensor with improved flexibility, sensitivity, and stability for use in a wearable device, and a method for manufacturing the same. Further, the following disclosure relates to a physical sensor for measuring a force applied from the outside, and more particularly, to a multi-directional physical sensor using a multi-layer microchannel array, which may sense all forces applied from the outside in three-dimensional directions such as a perpendicular direction and a parallel direction by applying the multi-layer microchannel array to a body having a three-dimensionally protruding shape.

BACKGROUND

Health care and health monitoring mean measurement of vital signs naturally generated from the body of a human, such as a pulse, a blood pressure, and respiration, or monitoring of motions of a human such as a motion of a joint of a finger, a toe, or the like, a walk, and the like. With an increasing interest of people in health and welfare in modern society, investment and development of a technology that utilizes a wearable device for smoothly performing the health care and health monitoring have been actively made for industrial purposes and academic purposes.

A sensor capable of measuring various physical quantities such as a force, a pressure, and a tensile strength is essential for measuring the vital signs and the body motion as described above. Further, there are many requirements for the sensor as a wearable device to enable the health monitoring, the first of which is flexibility (elasticity). The skin of a human is folded or stretched. That is, the skin of a human is subjected to various physical deformations such as stretching and folding. Therefore, for the use as a wearable device, the sensor needs to have flexibility and elasticity as physical properties to be stretchable and foldable like the skin. In a case in which a sufficient elasticity is not provided, the device may be damaged or an uncomfortable feeling may be caused when a user wears the device, which results in deterioration in utilization efficiency.

Second, a sufficient sensitivity needs to be guaranteed, such that the sensor may sense the vital signs. The vital signs such as a pulse and respiration are transferred through the skin. Therefore, a physical quantity of the pressure is very small, and thus the measurement is possible only with a high sensitivity with respect to a small pressure. Further, a sensor signal needs to be transmitted and received through wireless communication to implement an actual use of the sensor as a wearable device. In this case, when the sensitivity is low, the wireless communication may not be performed smoothly, and thus the utilization may become difficult.

Finally, stability of the sensor signal needs to be guaranteed. The wearable device is continuously used by the user in daily life. Therefore, a use frequency thereof is higher than that of other devices, and the wearable device is easily exposed to various external physical environments. In order to implement the sensor with a long life span, an initial value of the sensor signal needs to be stably maintained and stability for repetitive use needs to be ensured.

As such, studies and effort have been actively made to develop a sensor that satisfies the requirements for utilization as a wearable device, that is, flexibility, sensitivity, and stability. For example, a method of using a metal thin film by utilizing a structure capable of tolerating stretching, such as a serpentine pattern, or a method of changing resistance depending on stretching, pressurization, or the like by mixing a conductive material in a polymer are used. However, in the case of the first method, conductivity is high, but a tolerable stretching range is 30% or less, which is very limitative. In addition, peeling due to repetitive stretching and pressurization or the like results in a short life span. In the case of the second method, resistance is very high and viscoelasticity of the polymer itself is also shown in an electric signal as it is. Therefore, recovery of the signal is very slow, and strong hysteresis is shown.

To replace such methods, a study for manufacturing a sensor by using a conductive liquid that is suitably adapted even in a case of severe deformation and has a high conductivity has been actively conducted. Among the conductive liquids, a liquid metal has a high conductivity. However, the liquid metal also has a high surface tension, and thus a manufacturing method is complicated, and sensitivity is insufficient for use as a resistive pressure sensor. Studies of utilizing the liquid metal include Korean Patent Laid-Open Publication No. 10-2018-0102412 ("soft sensor using 3D printing, method for manufacturing the same, and wearable device including the same", published on Sep. 17, 2018, hereinafter, referred to as prior art). The prior art discloses a flexible sensor produced by injecting a conductive liquid metal on an elastic layer by using a syringe to form a microchannel. Particularly, in the prior art, a method of not using a mold is adopted to manufacture a flexible sensor with a smaller thickness, and the microchannel is 3D-printed by using a syringe, instead of using a lithography process for forming a microchannel as in the related art. In general, the lithography process requires various equipment and processing steps. Therefore, it is possible to greatly improve economical efficiency and productivity by not using the lithography process.

However, in a case of manufacturing a flexible sensor by using the method as the prior art, the thickness of the microchannel is determined by a surface tension of the liquid metal. Therefore, it is not possible to adjust the thickness of the microchannel as desired. In addition, there still is a limitation in sensitivity. That is, it is not possible to achieve a sufficiently high sensitivity, which is a problem of the sensor using the liquid metal described above. Therefore, improvement is still required.

Meanwhile, FIG. 21 illustrates a multi-directional force applied to a pressure sensor. As illustrated in FIG. 21, a pressure sensor 10 is exposed to various situations in which both a normal force (NF) in a direction perpendicular to a surface 11 and a shear force (SF) in a direction parallel to the surface 11 are applied. The normal force (NF) is a pressure component and is a measurement target considered at a design stage of the pressure sensor. However, in various actual utilizations, the shear force is applied together in addition to the normal force, such that a multi-directional force (MF) is caused.

The skin of a human body that serves as a pressure sensor actually has a function of sensing a shear force such as slip or friction, in addition to the normal force. Such a shear force provides various information which allows a person to recognize what kind of physical force is currently applied and to recognize an object. For example, the shear force provides information which allows a person to sense a pressure and occurrence of slip in a case where the person is in a lying state, and allows recognition of an object through various tactile impressions perceived with a finger, such as roughness. Further, information on the shear force in the parallel direction is also required in addition to the pressure, to enable a robot to perform a complex behavior as that of a human, for example, a behavior of gripping an object or a behavior of inserting any object.

FIGS. 22A-22F are diagrams illustrating a change of a sensed resistance depending on a magnitude and direction of a force applied to a general flexible pressure sensor 20.

The general flexible pressure sensor is operated on a principle like piezoresistance or piezocapacitance. In this case, a signal is changed depending on a given pressure. However, since the signal is changed also in a case where a direction in which a force is applied is different, it is not possible to identify whether the signal change is caused by a change in pressure or a change in direction of the force.

FIGS. 22A-22B and 22C-22D illustrate changes (darker color represents larger resistance change) in resistance sensed by the pressure sensor, the changes being caused by multi-directional forces (MFs) with different magnitudes (F1<F2) in the same direction (θ1). FIGS. 22C-22D and 22E-22F illustrate changes in resistance sensed by the pressure sensor, the changes being caused by multi-directional forces (MFs) with the same magnitude (F1) in different directions (θ1>θ2).

That is, in a case where forces with different magnitudes (F1<F2) are applied in the same direction (θ1), different resistance changes may be measured as illustrated in FIGS. 22A-22B and 22C-22D. However, in a case where forces with different magnitudes (F1<F2) are applied in different directions (θ1>θ2), the same resistance changes are measured as illustrated in FIGS. 22 and 22. Therefore, it is not possible to accurately sense a magnitude or direction of a force.

As such, when a multi-directional physical force is applied, it is difficult to measure a magnitude and directional component of the force. Therefore, development of a flexible force sensor capable of measuring a multi-directional physical force is demanded. Particularly, for use in a wearable device, there is a demand for development of a flexible force sensor that measures a multi-directional physical force by using liquid such as a liquid metal and has more excellent stability and mechanical properties, as compared with a physical sensor that uses a solid such as a functional nanopolymer and has high sensitivity and poor stability for long-term use.

SUMMARY

An embodiment of the present invention is directed to providing a flexible pressure sensor using a multi-material 3D-printed microchannel mold, the flexible pressure sensor being formed by using a conductive liquid and an elastomer, having a microchannel formed therein, and having improved flexibility, sensitivity, and stability in comparison to the related art. Another embodiment of the present invention is directed to providing a method for manufacturing a flexible pressure sensor using a multi-material 3D-printed microchannel mold, in which the flexible pressure sensor is manufactured by using the microchannel mold including microbumps, the microchannel mold being multi-material 3D-printed using a sacrificial material and a hard material.

Another embodiment of the present invention is directed to providing a multi-directional physical sensor using a multi-layer microchannel array, in which multi-layer microchannels are arranged in a lattice form in a body having a three-dimensionally and externally protruding shape such as a dome shape, such that both a normal force and a shear force may be sensed through a resistance change or capacitance change caused by a force applied to each channel, and a method for manufacturing the same.

In one general aspect, a flexible pressure sensor 100 using a multi-material 3D-printed microchannel mold includes: a flexible body 110 formed of an elastomer and in which a microchannel 115 is formed; and a conductive material 120 formed of a conductive liquid and filling the microchannel 115.

The flexible pressure sensor 100 may further include a plurality of microbumps 130 formed of a hard material and disposed to be in surface-contact with an upper surface or a lower surface of a part of the microchannel 115, wherein the flexible pressure sensor 100 measures a pressure by using a change of a resistance value of the conductive material 120 that is caused when the microchannel 115 filled with the conductive material 120 is deformed due to an external pressure, and the microbumps 130 prevent the external pressure from being dispersed over the flexible body 110 to increase a degree of the deformation of the microchannel 115.

Hereinafter, a direction in which the microchannel 115 extends will be referred to as an extending direction, a direction parallel to a thickness of the flexible pressure sensor 100 will be referred to as a thickness direction, and a direction perpendicular to the extending direction and the thickness direction and parallel to a width of the microchannel 115 will be referred to as a width direction.

The microchannel 115 may form a single route or multiple routes, and include a sensing portion S integrated in a predetermined shape at a predetermined position in the flexible body 110, and a reservoir V disposed to be spaced apart from the sensing portion S, positioned at a distal end of the route, having a cross-sectional area larger than that of the sensing portion S, and to which a signal line 125 for transmitting and receiving a signal to and from the outside is connected. The microbumps 130 may be formed on the sensing portion S of the microchannel 115. The sensing portion S of the microchannel 115 may be formed in a meandering channel shape. In the microchannel 115, a width or thickness of the reservoir V may be larger than a width or thickness of the sensing portion S.

Sensitivity of the flexible pressure sensor 100 may be adjusted by adjusting a ratio ($k_r=t/z$) of a thickness (t) of the microbump 130 to a thickness (z) between a surface of the flexible pressure sensor 100 that faces the microbump 130, and a surface of the microchannel 115 that faces the microbump 130, or by adjusting a ratio ($k_w = d/w$) of a width (d) of the microbump 130 to the width (w) of the microchannel 115.

The flexible pressure sensor 100 may have an embedded bump structure in which $k_t < 1$ and $k_w < 1$, an exposed bump structure in which $k_t \geq 1$, or an anchored bump structure in which $k_w \geq 1$.

As $k_t$ is increased, the sensitivity of the flexible pressure sensor 100 may be increased.

In a case in which $0 < k_w < 1$, as $k_w$ is increased, the sensitivity of the flexible pressure sensor 100 may be increased, and in a case in which $k_w \geq 1$, as $k_w$ is increased, the sensitivity of the flexible pressure sensor 100 may be decreased.

The microchannel 115 may include a connection portion T connecting the sensing portion S and the reservoir V, and the microbump 130 having the anchored bump structure may be formed in the connection portion T.

In another general aspect, a method for manufacturing the flexible pressure sensor 100 using a multi-material 3D-printed microchannel mold includes: a mold printing step of performing three-dimensional (3D)-printing of a micromold 140 having a 3D shape corresponding to a shape of the microchannel 115 by using a sacrificial material; a bump printing step of performing 3D-printing of the microbump 130 at a predetermined position on an upper surface of the micromold 140 by using a hard material; a primary body forming step of primarily coating a flexible material that is a material of the flexible body 110 on a substrate to form a flexible material layer; a mold disposing step of disposing a coupled body of the micromold 140 and the microbump 130 on an upper surface of the flexible material layer; a secondary body forming step of secondarily coating the flexible material on the flexible material layer and an upper surface of the coupled body and hardening the flexible material to form the flexible body 110 in which the coupled body is embedded; a channel forming step of forming the microchannel 115 in the flexible body 110 by removing the micromold 140; and a manufacturing completion step of filling the microchannel 115 with the conductive material 120 to complete manufacturing of the flexible pressure sensor 100.

In another general aspect, a pulse measurement system includes: the flexible pressure sensor 100 described above that is attached to a wrist of a user and measures a pulse; and three electrodes that are attached to a body of the user, measure an electrocardiogram (ECG), and include Ref, In+, and In−.

The pulse measurement system may calculate a blood pressure of the user by using a pulse transit time which is a difference between a pulse peak point and an electrocardiogram peak point.

In another general aspect, a body pressure distribution measurement system includes: a plurality of flexible pressure sensors 100 described above that are distributed on clothes of a user and perform pressure measurement; and a monitoring unit that performs real-time monitoring of a pressure applied to a body of the user by using a pressure measured by the plurality of flexible pressure sensors 100.

The flexible pressure sensors 100 may be distributed at positions corresponding to bony areas including shoulders, wing bones, elbows, knees, and a tailbone which are body parts that are likely to get a bedsore.

In another general aspect, a blood pressure estimation system including: the flexible pressure sensor 100 of claim 1 that is attached to a wrist of a user and measures a pulse; and three electrodes that are attached to a body of the user, measure an electrocardiogram (ECG), and include Ref, In+, and In−, wherein a blood pressure of the user is estimated by using a pulse transit time (PTT) which is a difference between a pulse peak point measured using the flexible pressure sensor 100 and an electrocardiogram peak point measured using the three electrodes.

In a flexible pressure sensor 1500 using a multi-material 3D-printed microchannel mold according to another embodiment of the present invention, the flexible body 1510 may include a protruding portion 1515 that protrudes outward, the microchannel 1520 may be disposed adjacent to an upper side of the flexible body 1510 along the protruding portion 1515, and include a plurality of unit channels 1521 having a predetermined length and arranged while being spaced apart from each other at a predetermined interval along a plane, and the unit channel 1521 may be bent along the plane so that opposite ends face different directions, respectively.

In a flexible pressure sensor 1100 using a multi-material 3D-printed microchannel mold according to another embodiment of the present invention, the flexible body 1110 may include a protruding portion 1115 that protrudes outward, the microchannel 1120 may include: a first channel 1121 including a plurality of first unit channels having a predetermined length and arranged while being spaced apart from each other at a predetermined interval along a plane; and a second channel 1122 disposed on the first channel 1121 and including a plurality of second unit channels having a predetermined length and arranged while being spaced apart from each other at a predetermined interval along the plane, the second unit channels intersecting with the first unit channels at a predetermined angle along the plane.

The multi-directional physical sensor may further include a plurality of bumps 1150 arranged on the first channel 1121 while being spaced apart from each other along the first channel 1121, wherein the bump 1150 has a hardness higher than that of the flexible body 1110.

The bump 1150 may be disposed at an intersecting portion between the first channel 1121 and the second channel 1122.

The first channel 1121 and the second channel 1122 may be orthogonal to each other along the plane.

The multi-directional physical sensor may further include a plurality of additional unit channels disposed on the second channel 1122, having a predetermined length, and arranged while being spaced apart from each other at a predetermined interval along the plane, wherein the additional unit channels are disposed in a state of being inclined with respect to the first unit channels and the second unit channels at a predetermined angle or more, respectively.

The flexible body 1110 may include a first body 1111*a* including the protruding portion 1115, formed at a lower side of the microchannel 1120, and supporting the microchannel 1120; and a second body 1111*b* covering an upper side of the microchannel 1120.

The flexible body 1110 may further include a filling material 1112 filled in a concave portion formed at a lower side of the protruding portion 1115 of the first body 1111*a*, wherein the filling material 1112 is formed of the same material as the first body 1111*a*, or a different material with a hardness different from that of the first body 1111*a*.

The microchannel 1120 or 1520 may be formed of a liquid metal.

The protruding portion 1115 or 1515 may have a three-dimensionally protruding shape.

In another general aspect, a method for manufacturing the multi-directional physical sensor using a multi-layer microchannel array includes: forming the first channel 1121 under the bump 1150 and filling a 1-1-st body 1111-1; manufacturing the multi-layer microchannel array by forming the second channel 1122 on the bump 1150 and filling the second body 1111b; forming a 1-2-nd body 1111-2 including the protruding portion 1150; and coupling the multi-layer microchannel array to an upper side of the 1-2-nd body 1111-2.

The forming of the first channel 1121 under the bump and the filling of the 1-1-st body 1111-1 may include: a first step (S01) of arranging a water-soluble mold 1125 having the same shape as the first channel 1121 and disposing the bump 1150 on an upper side of the water-soluble mold 1125; a second step (S02) of disposing the water-soluble mold 1125, on which the bump 1150 is disposed, on a base flexible body 1110a; a third step (S03) of filling the 1-1-st body 1111-1 in a liquid state on the base flexible body 1110a to embed the water-soluble mold 1125 on which the bump 1150 is disposed and hardening the 1-1-st body 1111-1; a fourth step (S04) of forming a first injection hole H1 in the 1-1-st body 1111-1 so that the water-soluble mold 1125 is in communication with the outside; a fifth step (S05) of forming a first channel space 1125a by injecting water into the first injection hole H1 to dissolve the water-soluble mold 1125; and a sixth step (S06) of forming the first channel 1121 by injecting a first channel material LM into the first injection hole H1 and hardening the first channel material LM.

The manufacturing of the multi-layer microchannel array by forming the second channel 1122 on the bump 1150 and filling the second body 1111b may include: a seventh step (S07) of disposing the 1-1-st body 1111-1 in which the first channel 1121 and the bump 1150 are embedded; an eighth step (S08) of disposing a water-soluble mold 1125 corresponding to the second channel 1122 on the 1-1-st body 1111-1, and filling and hardening the second body 1111b in a liquid state; a ninth step (S09) of forming a second injection hole H2 in the second body 1111b so that the water-soluble mold 1125 is in communication with the outside; a tenth step (S10) of forming a second channel space 1125b by injecting water into the second injection hole H2 to dissolve the water-soluble mold 1125; and an eleventh step (S11) of forming the second channel 1122 by injecting a second channel material LM into the second injection hole H2 and hardening the second channel material LM.

The forming of the 1-2-nd body 1111-2 including the protruding portion 1150 may include: a twelfth step (S12) of disposing the 1-2-nd body 1111-2 having a flat plate shape on a chamber 1200 that is hollow and has a convex portion forming hole 1210 formed in an upper portion of the chamber 1200; a thirteenth step (S13) of forming a convex portion 1115 in the 1-2-nd body 1111-2 by forming a negative pressure in the chamber 1200 with a vacuum pump 1250; and a fourteenth step (S14) of filling the concave portion formed at an upper side of the convex portion 1115 of the 1-2-nd body 1111-2 with the filling material 1112 and hardening the filling material 1112.

Other features and aspects will be apparent from the following detailed description, the drawings, and the claims.

BRIEF DESCRIPTION OF THE DRAWINGS

FIGS. 9A to 9D are diagrams for describing finite element analysis according to a thickness of a microbump.

DETAILED DESCRIPTION OF MAIN ELEMENTS

100: Flexible pressure sensor
110: Flexible body
115: Microchannel
120: Conductive material
125: Signal line
130: Microbump
140: Micromold
1100, 1500: Multi-directional physical sensor
1110, 1510: Flexible body
1110a: Base body
1111a: First body
1111-1: 1-1-st body
1111-2: 1-2-nd body
1111b: Second body
1112: Filling material
1115: Convex portion
1120, 1520: Microchannel
1521: Unit channel
1121: First channel
1122: Second channel
1125: Water-soluble mold
1125a: First channel space
1125b: Second channel space
1150: Bump
H1: First injection hole
H2: Second injection hole
1200: Chamber
1210: Convex portion forming hole
1250: Vacuum pump

DETAILED DESCRIPTION OF EMBODIMENTS

Hereinafter, a flexible pressure sensor using a multi-material 3D-printed microchannel mold according to the present invention with the above-described configuration, and a method for manufacturing the same will be described in detail with reference to the accompanying drawings.

[1] Flexible Pressure Sensor According to Present Invention

Figure 1:
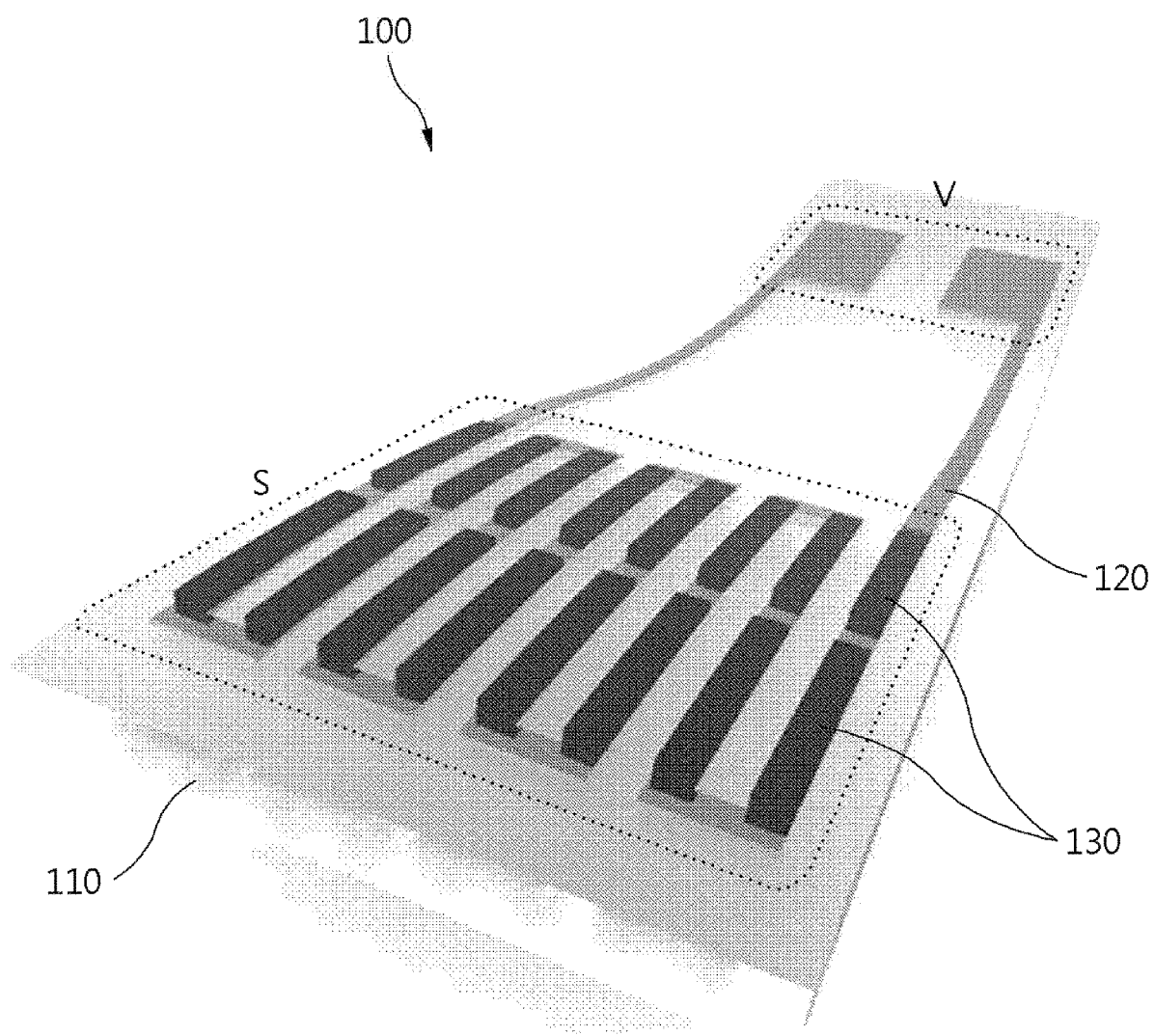
FIG. 1 illustrates a flexible pressure sensor according to the present invention.
Figure 2:
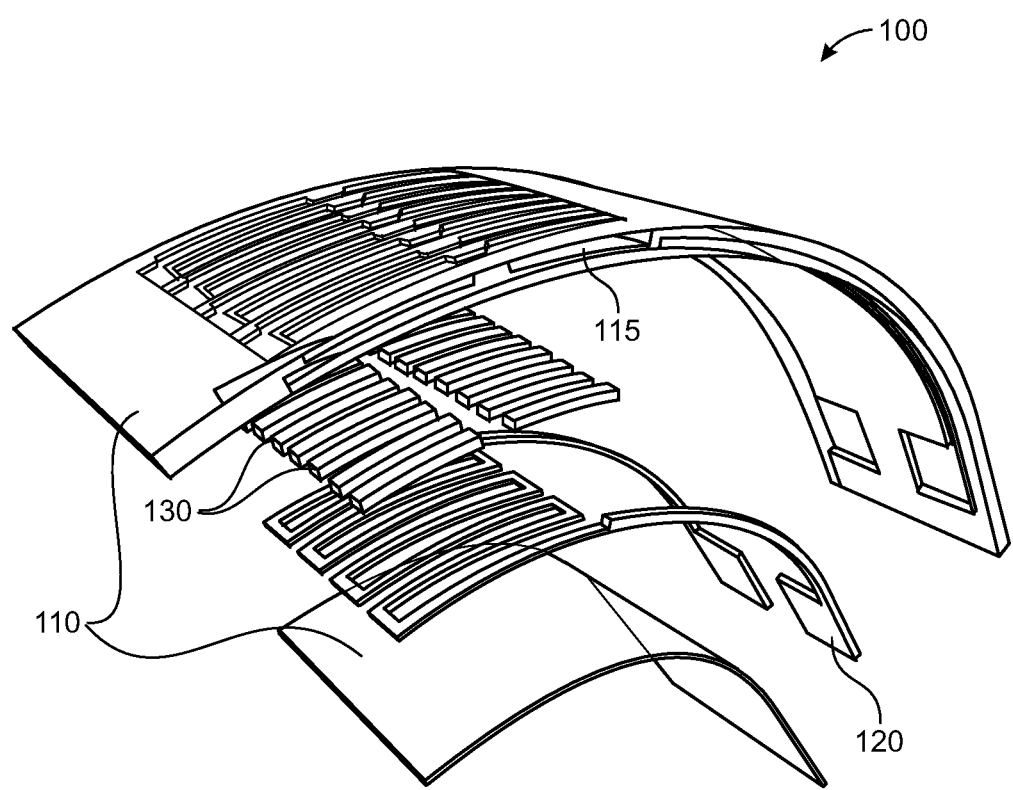
FIG. 2 is an exploded perspective view of the flexible pressure sensor according to the present invention.
Figure 3A:
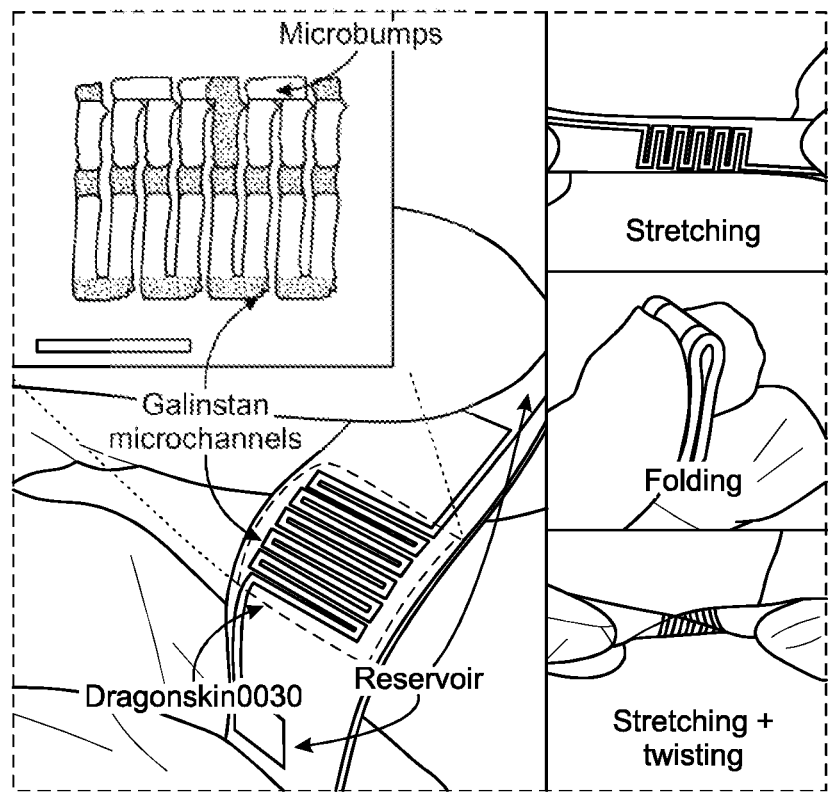
FIGS. 3A to 3C are photographs illustrating examples of the flexible pressure sensor according to the present invention.
Figure 3B:
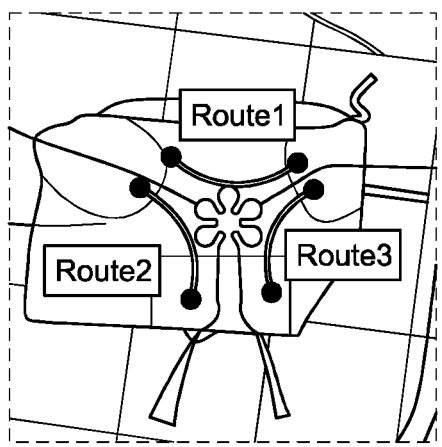
Figure 3C:
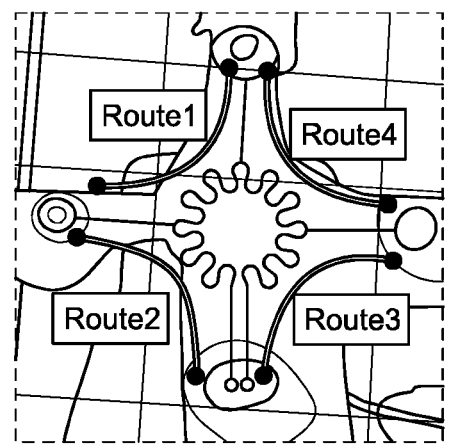

FIG. 1 illustrates an overall shape of a flexible pressure sensor according to the present invention, and FIG. 2 illustrates an exploded perspective view of the flexible pressure sensor according to the present invention. Further, FIGS. 3A to 3C are photographs illustrating examples of the flexible pressure sensor according to the present invention. As illustrated in FIGS. 1 and 2, a flexible pressure sensor 100 according to the present invention may include a flexible body 110 having a microchannel 115 formed therein, a conductive material 120, and microbumps 130. Hereinafter, the respective components will be described in more detail.

The flexible body 110 refers to the whole body of the flexible pressure sensor 100 that is formed of a flexible material to be applicable to a wearable device. As illustrated in FIG. 3A, the flexible body 110 is formed of an elastomer having a high flexibility to smoothly cope with various deformations such as stretching, folding, and twisting. Further, the flexible body 110 has the microchannel 115 formed therein and has a planar shape for convenience of attachment to the body, clothes, or the like.

The microchannel 115 may form a single route or multiple route as illustrated, and may include a sensing portion S and a reservoir V. FIG. 3A is a photograph illustrating an example in which the microchannel 115 forms a single route, and FIG. 3B is a photograph illustrating an example in which the microchannel 115 forms multiple routes. The sensing portion S is integrated in a predetermined shape at a predetermined position in the flexible body 110. For example, the sensing portion S may be formed in a meandering channel shape as illustrated in FIG. 3A. It is a matter of course that the present invention is not limited thereto. The sensing portion S may have any shape suitable for needs and purposes, such as a spiral shape, an unfolded petal shape as illustrated in FIG. 3B, or a shape in which the sensing portion S is integrated over multiple sections. The reservoir V is disposed to be spaced apart from the sensing portion S, positioned at a distal end of the route, having a cross-sectional area larger than that of the sensing portion S, and to which a signal line 125 for transmitting and receiving a signal to and from the outside is connected. In FIGS. 1 and 2, a case in which the sensing portion S is formed on one side of the flexible pressure sensor 100 and the reservoir V is formed on the other side is illustrated. However, the present invention is not limited thereto. That is, various modifications are possible. For example, the sensing portion S may be formed at a central portion of the flexible pressure sensor 100 and the reservoir V may be formed on each of opposite end portions of the flexible pressure sensor 100. Alternatively, in a case of the example in which the microchannel 115 forms multiple routes as illustrated in FIG. 3B, the sensing portion S may be formed at a central portion of the flexible pressure sensor 100 and the reservoir V may be formed on each end portion of multiple routes.

The conductive material 120 is formed of a conductive liquid and fills the microchannel 115 to actually measure a pressure. The conductive liquid may be a liquid metal as a specific example. The liquid metal refers to a metal that is present in a liquid state at room temperature, such as mercury. The liquid metal has a high conductivity and thus may drive a sensor with low power. In addition, the liquid metal is well adapted even in a case of various physical deformations, and thus an electric property thereof is not lost. That is, a sensor manufactured in a form in which the conductive material 120 formed of the conductive liquid fills the microchannel 115 in the flexible body 110 is highly suitable as a wearable sensor, because a performance difference such as a change in basic resistance does not occur even in a case of various physical deformations such as stretching, folding, and twisting.

The microbump 130 is formed of a hard material. A plurality of microbumps 130 are disposed so as to be in surface-contact with an upper surface or a lower surface of a part of the microchannel 115. In the drawings of the present specification, a case in which the microbumps 130 are disposed on the upper surface of the microchannel 115 and an external pressure is applied from above is illustrated. However, it is a matter of course that the microbumps 130 may be disposed on the lower surface of the microchannel 115 in a case in which the external pressure is applied from below. Here, the hard material refers to a material that is solid. The hard material is not deformed even when an external pressure is applied, unlike the flexible body 110 that is formed of a flexible material and deformed when the external pressure is applied. Further, the expression "micro" in the term "microbump" means that the microbump 130 corresponds to the microchannel 115, and the expression "bump" (which will be described later in more detail) means an agglomerate formed on each of portions of the microchannel 115.

The flexible pressure sensor 100 is configured to measure a pressure by using a change of a resistance value of the conductive material 120 that is caused when the microchannel 115 filled with the conductive material 120 is deformed due to an external pressure. A sensor only including the flexible body 110 and the conductive material 120 according to the related art has been developed. However, in the sensor according to the related art, resistance is not greatly changed by a small pressure, which is disadvantageous. However, according to the present invention, the microbumps 130 prevent the external pressure from being dispersed over the flexible body 110, and thus a degree of the deformation of the microchannel 115 is increased. Therefore, it is possible to solve such a problem of the related art and greatly improve the sensitivity of the sensor. In consideration of such use, it is preferable that the microbumps 130 are formed on the sensing portion S of the microchannel 115.

Figure 4A:
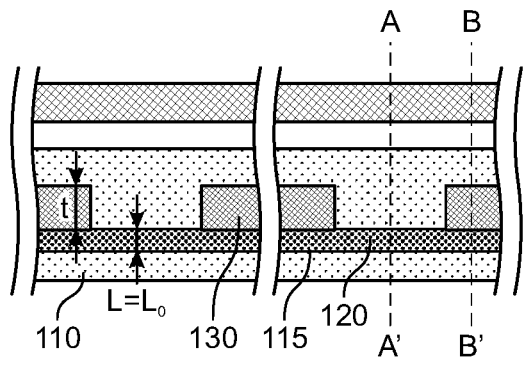
FIGS. 4A-4F are views for describing an operational principle of the flexible pressure sensor according to the present invention.
Figure 4B:
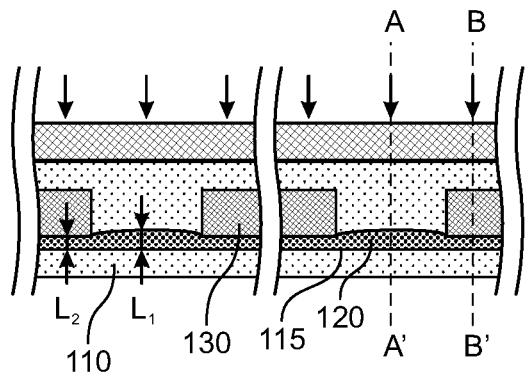
Figure 4C:
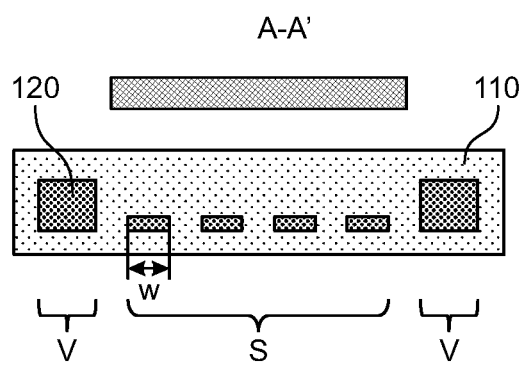
Figure 4D:
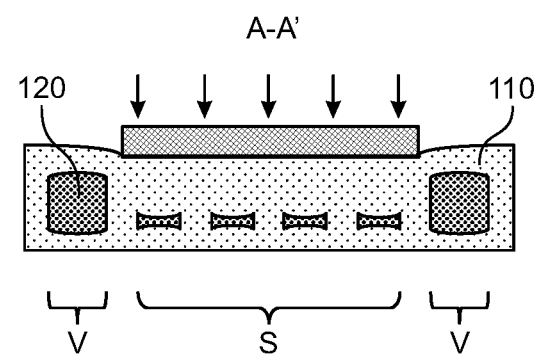
Figure 4E:
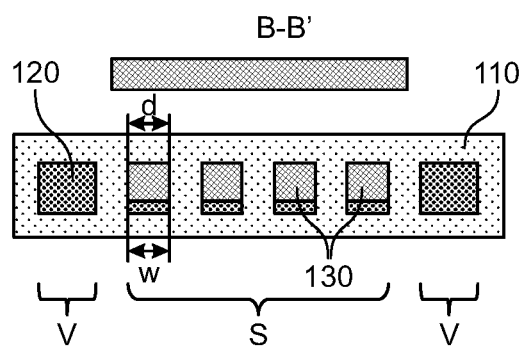
Figure 4F:
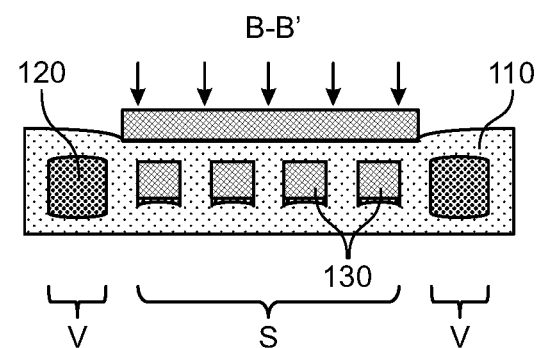

FIGS. 4A-4F are views for describing an operational principle of the flexible pressure sensor according to the present invention. Hereinafter, a direction in which the microchannel 115 extends will be referred to as an extending direction, a direction parallel to a thickness of the flexible pressure sensor 100 will be referred to as a thickness direction, and a direction perpendicular to the extending direction and the thickness direction and parallel to a width of the microchannel 115 will be referred to as a width direction. Here, views on the uppermost side of FIGS. 4A-4F are views of a part of the microchannel 115 on which the microbump 130 are disposed, taken along the extending direction, and views of FIGS. 4C and 4D are cross-sectional views of the part of the microchannel 115 taken along line A-A', and views of FIGS. 4E and 4F are cross-sectional views of the part of the microchannel 115 taken along line B-B'.

FIGS. 4A, 4C and 4E illustrate a state in which an external pressure is not applied to the flexible pressure sensor 100. As illustrated in the view on the uppermost side of FIG. 4A, a thickness of the microchannel 115 at a region corresponding to the sensing portion S is L, and a thickness of the microbump 130 is t. The thickness of the microchannel 115 is changed depending on whether or not a pressure is applied, and a thickness of the microchannel 115 in an original state, that is, the thickness of the microchannel 115 in a state in which no pressure is applied is $L_0$. Further, as illustrated in the views of FIGS. 4C and 4E, a width of the microchannel 115 at the region corresponding to the sensing portion S is w, and a width of the microbump 130 is d. Here, a cross-sectional area A of the microchannel 115 is obtained by multiplying the width by the thickness (that is, wL). Further, although not illustrated, an overall length of the microchannel 115 corresponding to the sensing portion S is l.

In addition, as described above, the reservoir V is positioned at a distal end of a single route or each of multiple routes formed by the microchannel 115, and has a cross-sectional area larger than that of the sensing portion S. That is, specifically, the width or thickness of the reservoir V may be larger than the width or thickness of the sensing portion S. FIGS. 4A-4F illustrate an example in which both of the width and the thickness of the reservoir V are larger than the width and the thickness of the sensing portion S as illustrated in the views on the middle side and the lowermost side. FIGS. 1 and 2 illustrate an example in which the reservoir V and the sensing portion S have the same thickness, but the width of the reservoir V is larger than the width of the sensing portion S.

FIGS. 4B, 4D and 4F illustrate a state in which an external pressure is applied to the flexible pressure sensor 100. Once an external pressure is applied to the flexible pressure sensor 100, as illustrated in FIG. 4B, a portion to which the pressure is applied, that is, the region corresponding to the sensing portion S of the flexible pressure sensor 100 is compressed and deformed, and naturally, the microchannel 115 in the region corresponding to the sensing portion S is also compressed and deformed. Therefore, as illustrated in the views of FIGS. 4D and 4F, the conductive material 120 in the microchannel 115 in the region corresponding to the sensing portion S flows to a portion to which no pressure is applied, that is, to a region corresponding to the reservoir V. Therefore, the region corresponding to the reservoir V is expanded and deformed when the region corresponding to the sensing portion S is compressed and deformed. That is, since the microchannel 115 itself forms a closed surface as a single route or multiple route, an overall volume is not changed. However, as the region corresponding to the sensing portion is compressed and deformed, an amount of the conductive material 120 in the microchannel 115 in the region corresponding to the sensing portion S is definitely changed.

As such, in a case in which the pressure is removed in a state in which the pressure is applied to the region corresponding to the sensing portion S, the region corresponding to the sensing portion is compressed and deformed, and the region corresponding to the reservoir V is expanded and deformed, the conductive material 120 formed of the conductive liquid concentrated in the reservoir V due to an internal pressure of the microchannel 115 appropriately returns to the sensing portion S, such that the flexible pressure sensor 100 is restored to an original state as illustrated in FIG. 4A.

Resistance is determined based on a length and a cross-sectional area of a resistor. As described above, the length l of the microchannel 115 may be regarded as a value that is not changed, and the cross-sectional area A of the microchannel 115 may be wL. That is, resistance R of the region corresponding to the sensing portion S may be calculated by the following Equation.

$$R = \rho l/A = \rho l/wL$$

(R: resistance, ρ: resistivity constant of the material, l: length, A: cross-sectional area, w: width, and L: thickness)

Here, in a case in which the thickness of the microchannel 115 when no pressure is applied is $L_0$, a thickness of a portion of the microchannel 115 where the microbump 130 is not positioned when a pressure is applied is $L_1$, and a thickness of a portion of the microchannel 115 where the microbump 130 is positioned when the pressure is applied is $L_2$, the following relationship is established between these three thicknesses.

$$L_0 > L_1 > L_2$$

As such, in the flexible pressure sensor 100 according to the present invention, the thickness of the microchannel 115 is drastically changed to $L_1$ or $L_2$ when an external pressure is applied, and accordingly, the resistance change depending on the pressure change becomes more drastic.

FIGS. 5A to 5E illustrate comparison between the flexible pressure sensor 100 according to the present invention, that is, the flexible pressure sensor 100 with the microbump 130 and a flexible pressure sensor without the microbump 130 according to the related art.

In a case in which the flexible pressure sensor 100 does not include the microbump 130, that is, in a case of the sensor using the liquid metal according to the related art, an external energy is used to deform an elastomer and move a fluid. Therefore, the energy is consumed due to viscoelasticity of the elastomer itself, and thus an internal cross-sectional area is not greatly changed. As a result, a problem that resistance is not greatly changed by a small pressure, that is, a problem that sensitivity is low occurs.

However, according to the present invention, the microbump 130 formed of the hard material is in surface-contact with the microchannel 115 filled with the conductive material 120 formed of the conductive liquid. Therefore, it is possible to prevent the external pressure from being dispersed over the flexible body 110 formed of the elastomer as much as possible, and the whole pressure may be used to decrease the cross-sectional area of the microchannel 115.

Figure 5A:
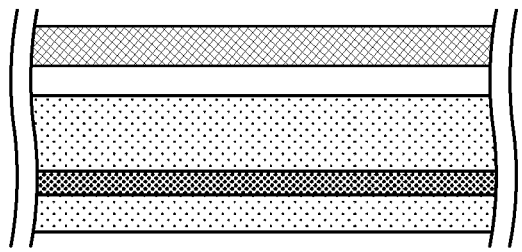
FIGS. 5A to 5E illustrate comparison between the flexible pressure sensor according to the present invention and a flexible pressure sensor according to the related art.
Figure 5B:
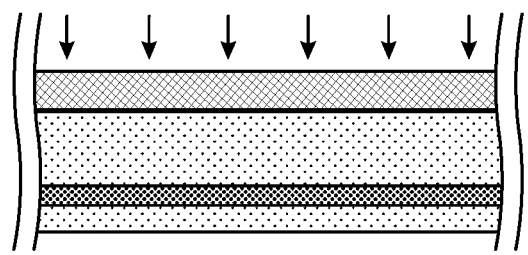
Figure 5C:
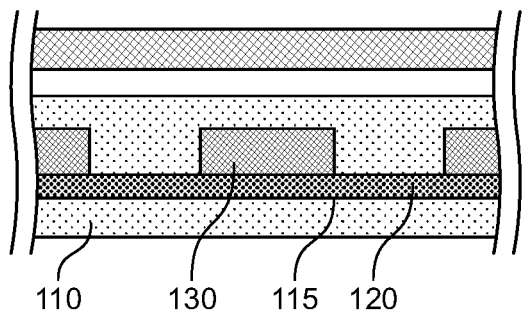
Figure 5D:
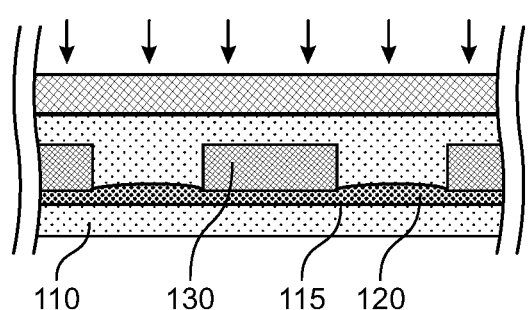
Figure 5E:
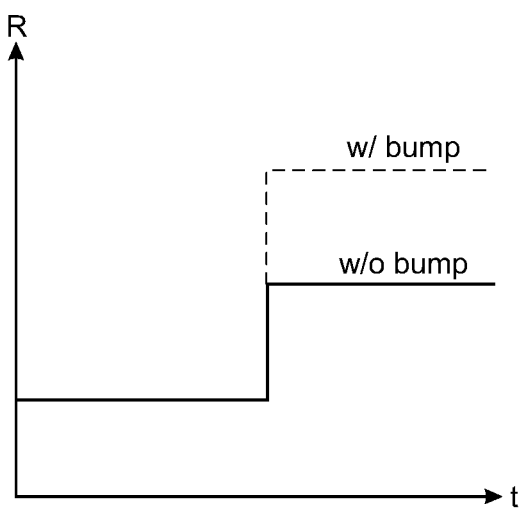
Figure 6:
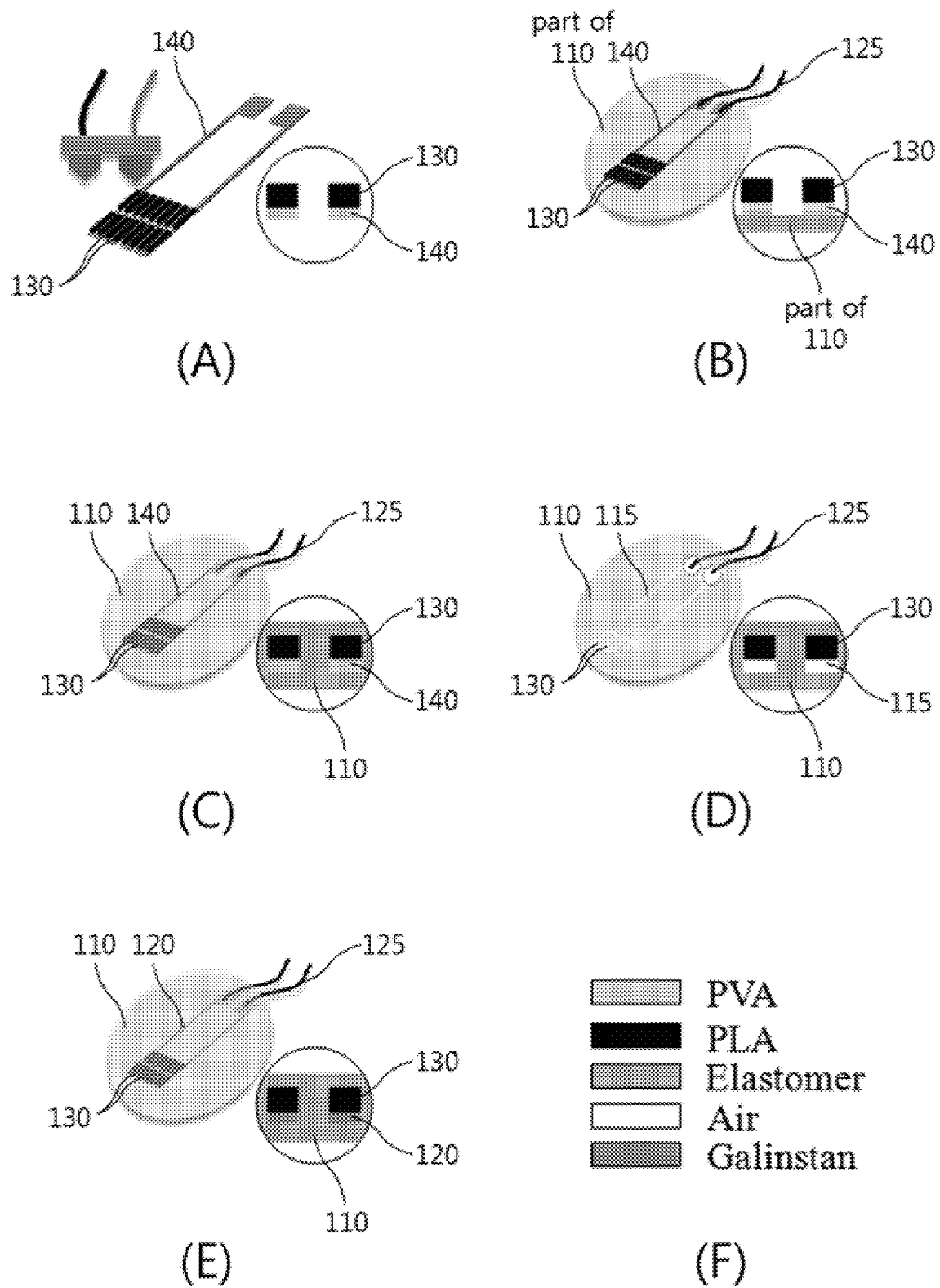
FIGS. 6A to 6F illustrate a method for manufacturing a flexible pressure sensor according to the present invention.

FIGS. 5A and 5C illustrate the sensor according to the related art, FIGS. 5B and 5D illustrate the flexible pressure sensor 100 according to the present invention, and FIG. 5E illustrates a change of the resistance R with respect to time t in each of the sensor according to the related art and the flexible pressure sensor 100 according to the present invention. It is seen that the resistance change is more drastic in the flexible pressure sensor 100 with the microbump 130 according to the present invention (w/bump), in comparison to the flexible pressure sensor without the microbump 130 according to the related art (w/o bump) as illustrated in FIG. 5E. That is, it may be appreciated that as the flexible pressure sensor 100 according of the present invention includes the microbump 130, the sensitivity may be greatly improved as compared with the sensor according to the related art.

Figure 7A:
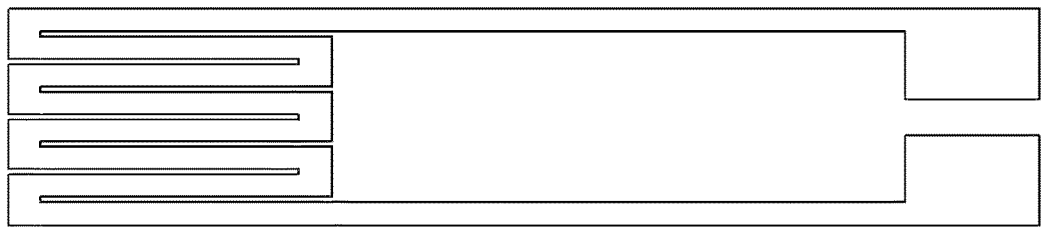
FIGS. 7A to 7C are photographs illustrating manufacturing examples of the flexible pressure sensor according to the present invention.
Figure 7A:
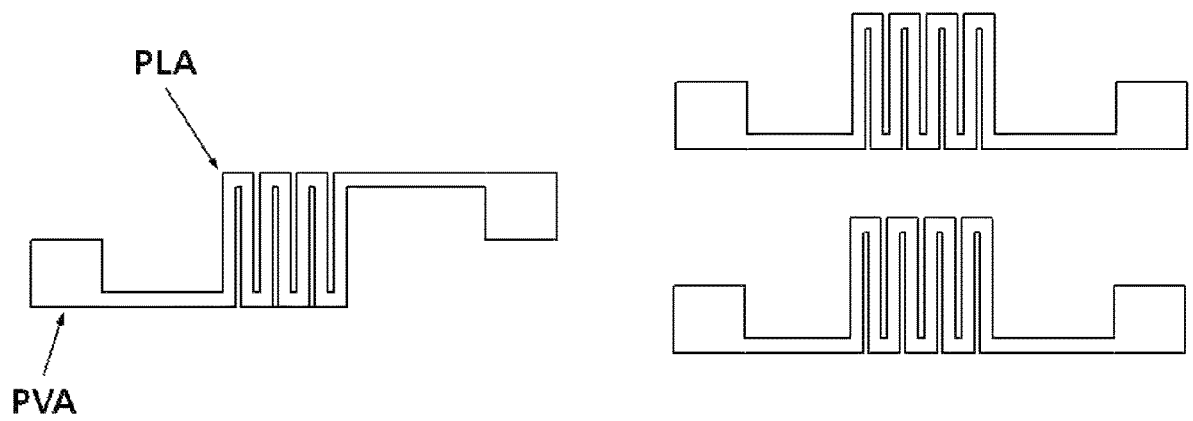
Figure 7B:
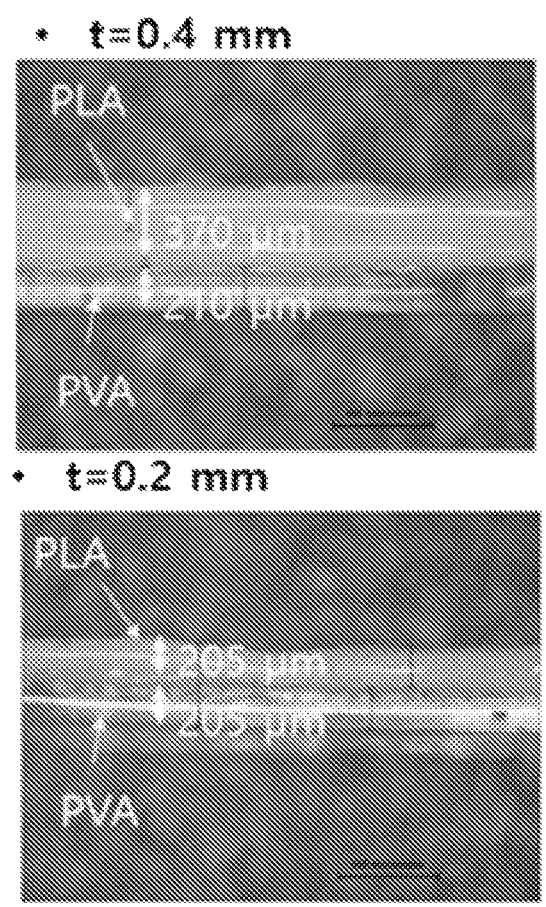
Figure 7C:
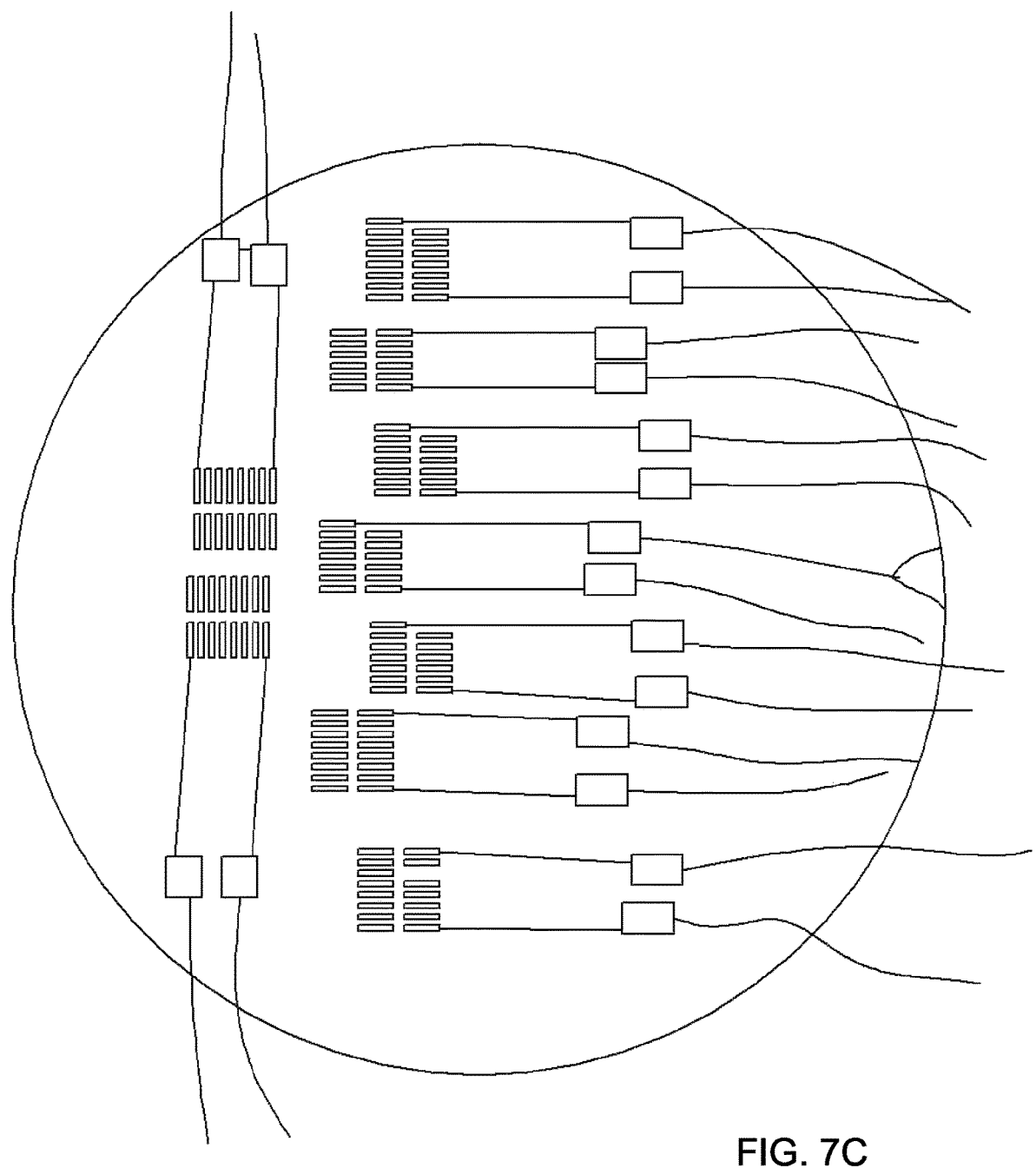

[2] Method for Manufacturing Flexible Pressure Sensor According to Present Invention FIGS. 6A to 6F schematically illustrate a method for manufacturing the flexible pressure sensor according to the present invention, and FIGS. 7A to 7C are photographs illustrating manufacturing examples of the flexible pressure sensor according to the present invention. Steps of the method for manufacturing the flexible pressure sensor according to the present invention will be described as follows with reference to FIGS. 6A to 7C.

FIG. 6A illustrates both of a mold printing step and a bump printing step. As illustrated in FIG. 6A, in the mold printing step, a micromold 140 having a three-dimensional shape corresponding to the shape of the microchannel 115 is 3D-printed using the sacrificial material. Next, in the bump printing step, the microbump 130 is 3D-printed at a predetermined position on an upper surface of the micromold 140 by using the hard material. The micromold 140 is to be removed later, and thus it is preferable that the micromold 140 is formed of an easy-to-remove material such as a water-soluble material.

For example, a dual nozzle FDM 3D printing method may be used, in which a water-soluble polyvinyl alcohol (PVA) filament may be printed from a nozzle for manufacturing the micromold 140, and a polylactic acid (PLA) filament which is a material with high hardness may be printed from the other nozzle for manufacturing the microbump 130. The soluble filament serves to form the shape of the microchannel into which the conductive liquid is to be inserted, and the hard filament serves as the microbump for increasing the sensitivity of the sensor. For reference, FIG. 6F illustrates examples of the materials used for each component.

FIG. 7A is a photograph illustrating examples of a coupled body of the micromold 140 and the microbump 130 that are formed by performing the mold printing step and the bump printing step, respectively, when viewed from above. As illustrated, the coupled body may be designed and manufactured in various sizes and shapes for various needs such as a case of measuring a pressure of a large area such as a body part, or a case of measuring a small area, for example, measuring a pulse. FIG. 7B is photograph illustrating cross sections of examples of the coupled body of the micromold 140 and the microbump 130. It may be seen that it is possible to smoothly manufacture a very thin and elaborate object by using 3D printing.

FIG. 6B illustrates both of a primary body forming step and a mold disposing step. As illustrated in FIG. 6B, in the primary body forming step, a flexible material that is the material of the flexible body 110 is primarily coated on a substrate to form a flexible material layer. Next, in the mold disposing step, the coupled body of the micromold 140 and the microbump 130 is disposed on an upper surface of the flexible material layer. In this step, it is preferable that the signal line 125 is disposed at a portion corresponding to the reservoir V of the micromold 140.

FIG. 6C illustrates a secondary body forming step. In the secondary body forming step, the flexible material is secondarily coated on the flexible material layer and an upper surface of the coupled body and hardened to form the flexible body 110 in which the coupled body is embedded. As such, the coupled body may be smoothly embedded in the flexible body 110 by sequentially performing the primary body forming step and the secondary body forming step. FIG. 7C is a photograph illustrating an example of a step of manufacturing a flexible body in which multiple coupled body are embedded.

FIG. 6D illustrates a channel forming step, and in the channel forming step, the micromold 140 is removed and the microchannel 115 is formed in the flexible body 110. As described above, the micromold 140 is formed of an easy-to-remove material such as the PVA filament. Therefore, the micromold 140 may be easily removed by forming a small hole in one side of the flexible body 110 in which the coupled body is embedded, and injecting a solvent of the micromold 140 through the hole. Once the micromold 140 is removed as described above, a space in which the micromold 140 has been present becomes empty, and the empty space serves as the microchannel 115.

FIG. 6E illustrates a manufacturing completion step, and in the manufacturing completion step, the microchannel 115 is filled with the conductive material 120, thereby completing the manufacturing of the flexible pressure sensor 100. More specifically, the conductive material 120 is injected through the hole formed for the removal of the micromold 140 as described above and the hole is stopped, thereby completing the manufacturing of the sensor. As described above, the conductive material 120 is most preferably a conductive liquid. For example, the conductive material 120 may be galinstan which is one of the liquid metals. The galinstan is an alloy of gallium, indium, and tin, is harmless to the human body, and has a high electric conductivity. Therefore, the galinstan is significantly suitable for use in such a sensor utilizing a conductive liquid. Meanwhile, in a case in which multiple coupled bodies are embedded in one elastomer layer as illustrated in FIG. 7C, a step of appropriately determining a shape of the flexible body 110 by appropriately cutting the elastomer layer may be further performed later.

Figure 8:
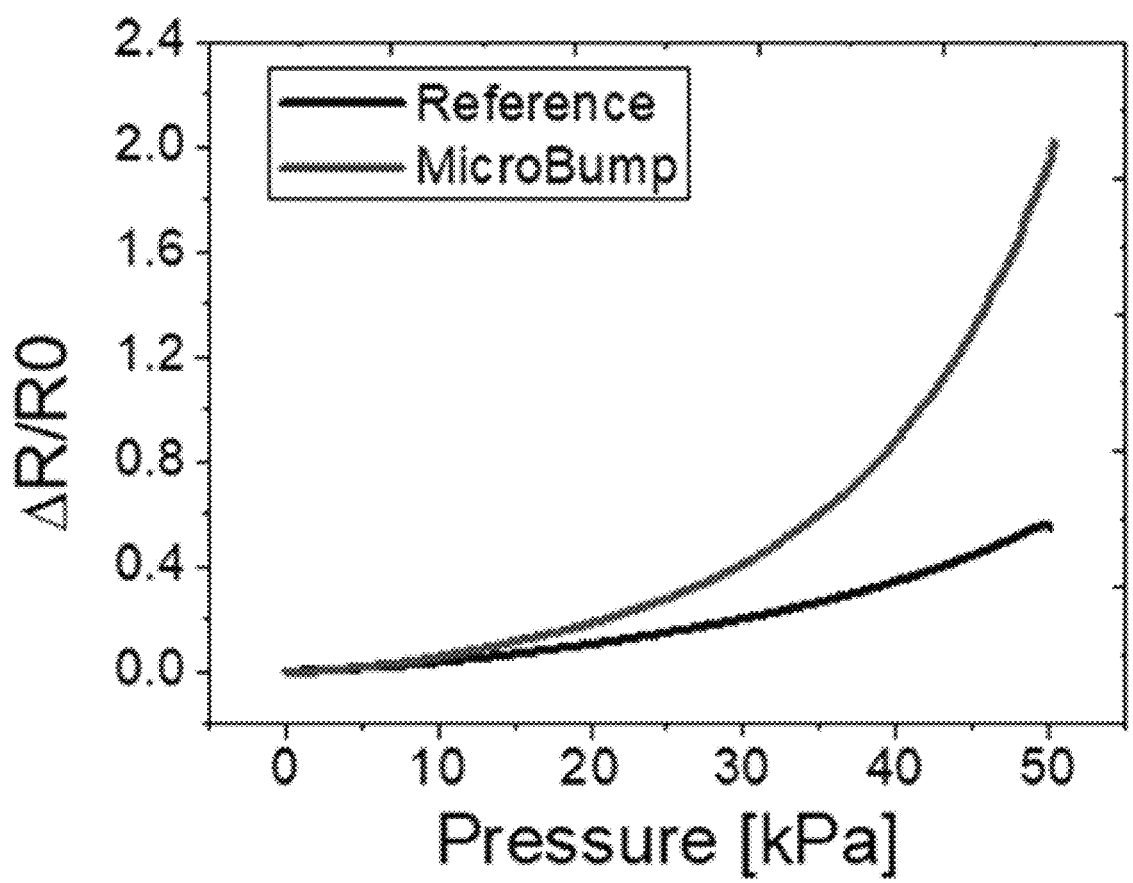
FIG. 8 illustrates a result of a comparison experiment on the flexible pressure sensor according to the present invention and a flexible pressure sensor according to the related art.

[3] Result of Experiment on Flexible Pressure Sensor According to Present Invention FIG. 8 illustrates a result of a comparison experiment on the flexible pressure sensor according to the present invention and the flexible pressure sensor according to the related art. As a result of observing a resistance change with respect to a pressure, when a pressure of 50 kPa is applied, the resistance increased by 0.5 times in the sensor (the sensor according to the related art) without the microbump, but the resistance increased by two times in the sensor (the sensor according to the present invention) with the microbump as illustrated in FIG. 8. Therefore, it can be appreciated that the sensitivity increased by four times. As theoretically and briefly described above, the result of FIG. 8 clearly shows that the sensitivity of the flexible pressure sensor 100 according to the present invention is much higher than that of the sensor according to the related art.

Figure 9A:
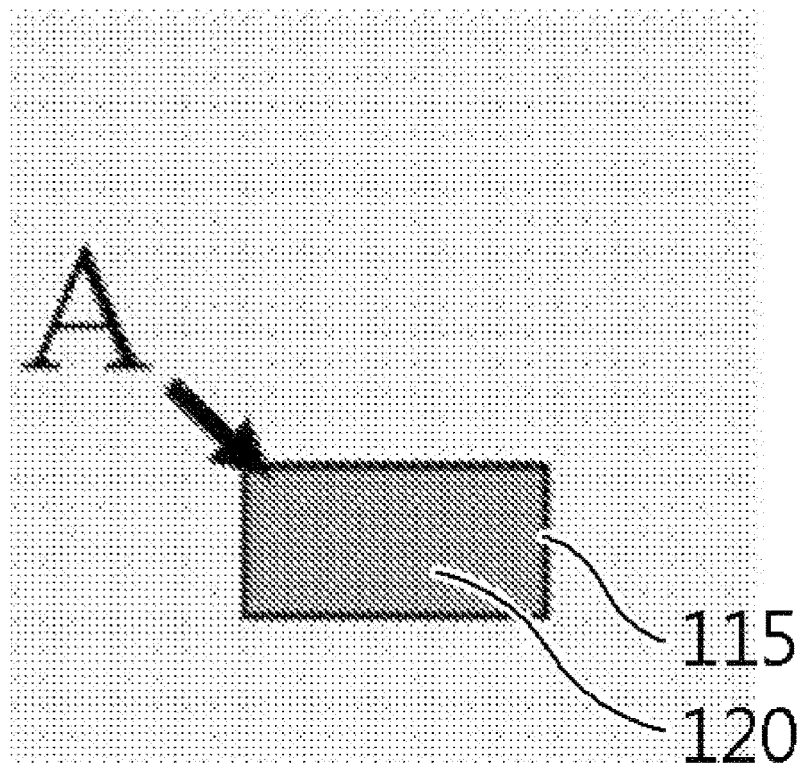
Figure 9A:
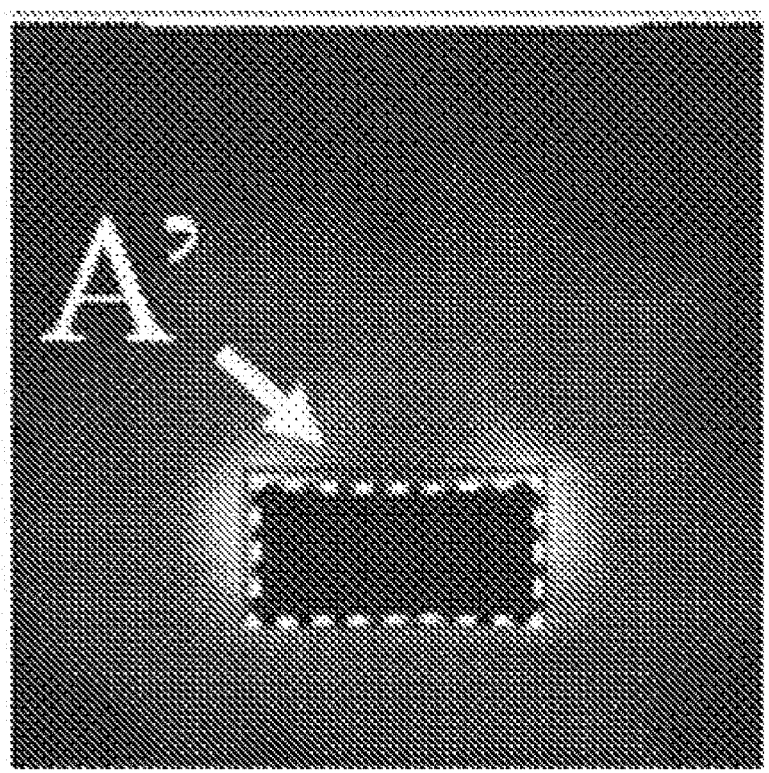
Figure 9B:
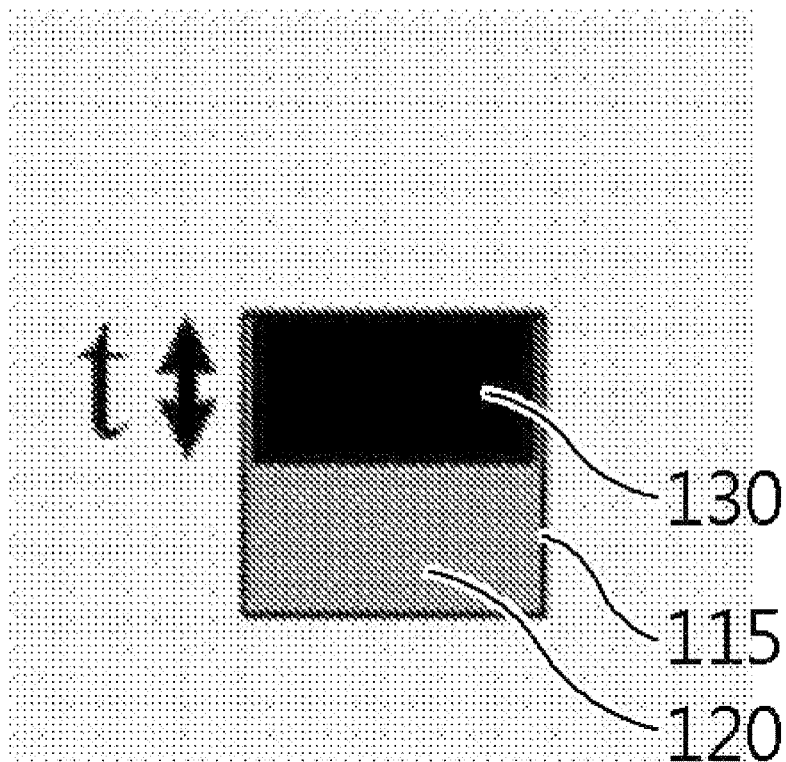
Figure 9B:
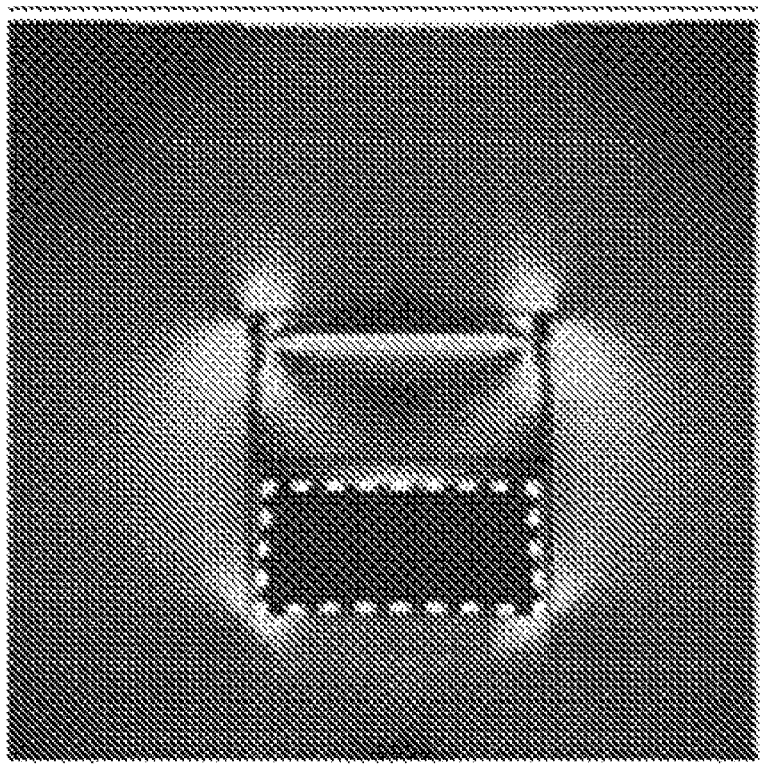

FIGS. 9A to 9D are diagrams for describing finite element analysis according to the thickness of the microbump, which illustrate a result of performing a finite element analysis simulation to more certainly analyze the above-described sensitivity improvement effect. FIG. 9A illustrates a case in which no microbump is present, FIG. 9B illustrates a case in which the thickness t of the microbump is 200 µm, and FIG. 9C illustrates a case in which the thickness t of the microbump is 400 µm. Further, cross-sectional area changes when a pressure is applied in the respective cases are illustrated. As shown in a table of FIG. 9D, it may be appreciated that a decrease in cross-sectional area (an increase in resistance) was more significant in a case in which the microbump is present, than in a case in which no microbump is present. Further, the larger the thickness of the microbump was, the more significant the decrease in cross-sectional area (the increase in resistance) was. As may be inferred from such a simulation result, a larger thickness t of the microbump 130 is preferred to increase an influence of the microbump 130. However, in a case in which the thickness t of the microbump 130 is excessively large, the thickness of the flexible pressure sensor 100 may become unnecessarily large. In other words, it is preferable that the thickness t of the microbump 130 is appropriately determined to be the same as, larger than, or smaller than the thickness L of the microchannel 115, in consideration of both of the increase in resistance and the thickness of the sensor.

Figure 10:
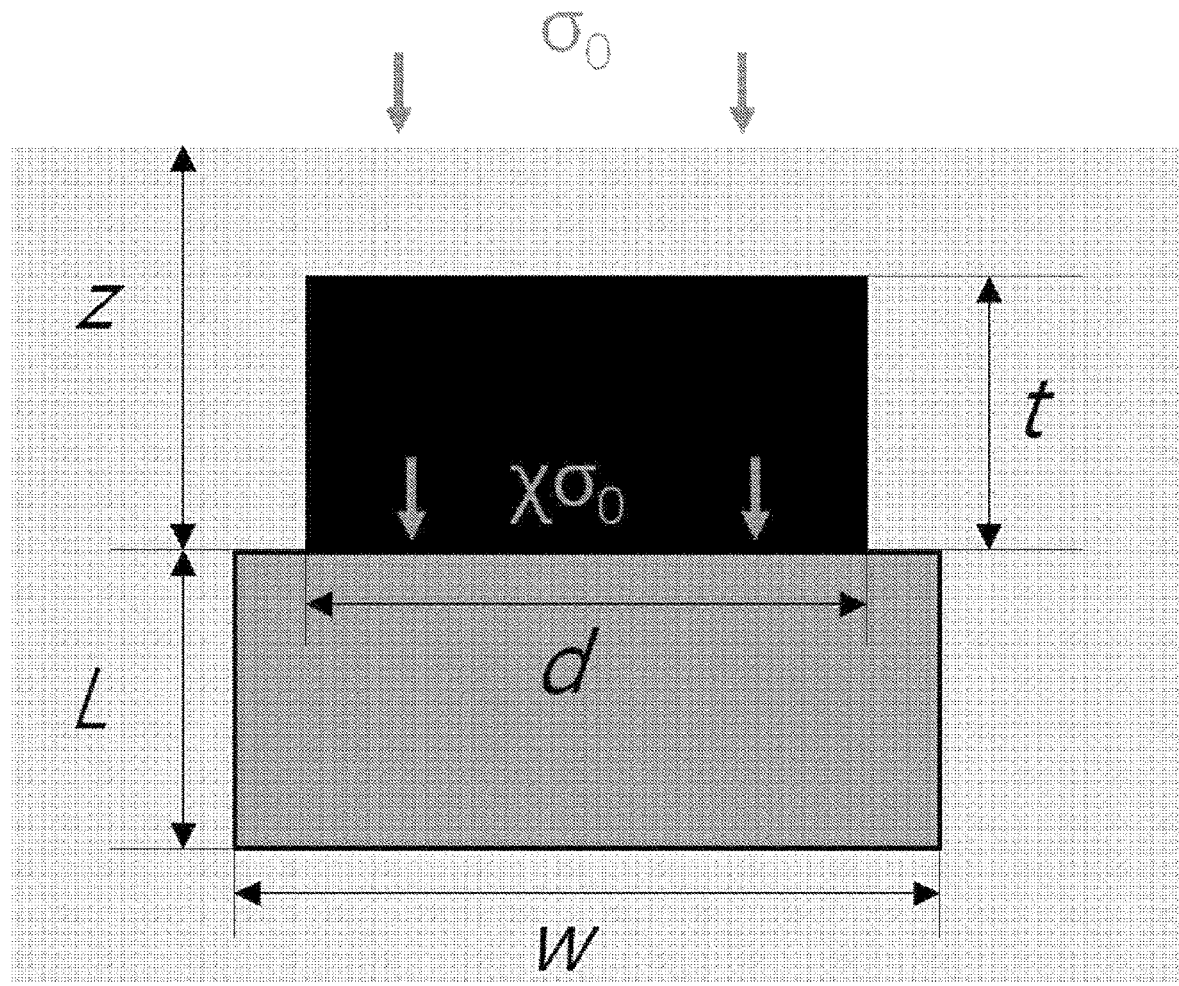
FIG. 10 illustrates a structure definition of the flexible pressure sensor according to the present invention.
Figure 11A:
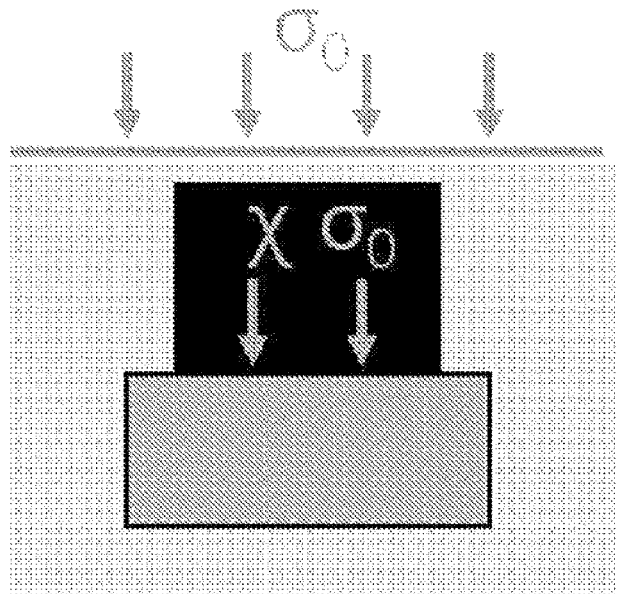
FIGS. 11A to 11C illustrate various types of microbump structures according to various values of $k_t$ and $k_w$.
Figure 11B:
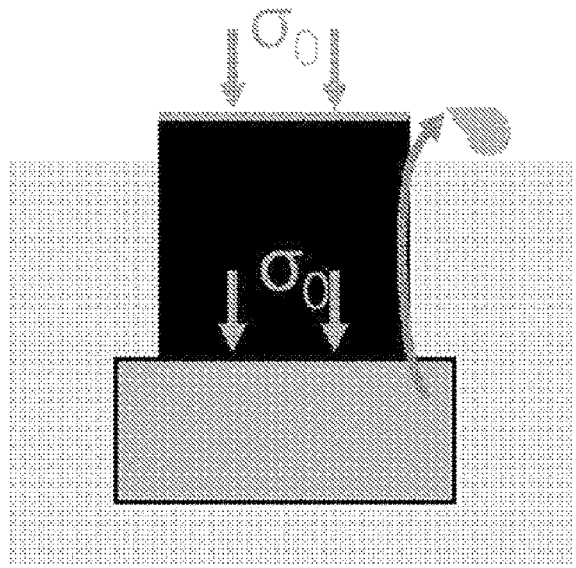
Figure 11C:
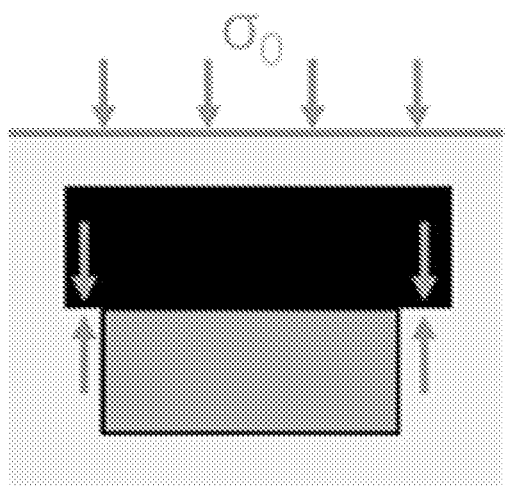

As described above, the thickness t of the microbump 130, the width d of the microbump 130, the width w of the microchannel 115, and the thickness of the flexible pressure sensor 100 itself affect one another. Therefore, to more specifically define a relationship therebetween, FIG. 10 illustrates a structure definition of the flexible pressure sensor according to the present invention, and an experiment was conducted. Signs of respective parts illustrated in FIG. 10 and a relationship therebetween are as follows.

t: thickness of microbump
d: width of microbump
L: thickness of microchannel
w: width of microchannel
z: thickness between microbump-side sensor surface and microbump-side channel surface
$k_t=t/z$
$k_w=d/w$
$\sigma_0$: pressure applied to microbump-side sensor surface
$\chi$: ratio of pressure transferred to microchannel FIGS. 11A to 11C illustrate various types of microbump structures according to various values of $k_t$ and $k_w$.

FIG. 11A illustrates an embedded bump structure, in which the microbump 130 is completely embedded in the flexible body 110 ($k_t<1$), and the width d of the microbump 130 is smaller than the width w of the microchannel 115 ($k_w<1$). In this case, a pressure actually transferred to the microchannel is smaller than a pressure ($\sigma_0$) applied to the microbump-side sensor surface ($\chi<1$). Such a structure is significantly stable, and thus may be widely used.

Meanwhile, FIG. 11B illustrates an exposed bump structure, in which the microbump 130 is exposed from the flexible body 110 ($k_t=1$) or protrudes from the flexible body 110 ($k_t>1$) so that an external pressure is directly applied to the microbump 130 ($k_t\geq1$). In this case, the external pressure applied to the microbump 130 is transferred to the microchannel 115 as it is, and thus the ratio of transferred pressure is 1 ($\chi=1$). FIG. 11C illustrates an anchored bump structure, in which the width d of the microbump 130 is the same as or larger than the width w of the microchannel 115 ($k_w\geq1$).

In the above description, the wide use is enabled by applying the embedded bump structure of FIG. 11A to the flexible pressure sensor 100. However, in a case in which there is a special need, an appropriate design change may be made for the need by appropriately mixing the exposed bump structure of FIG. 11B and the anchored bump structure of FIG. 11C.

Figure 12:
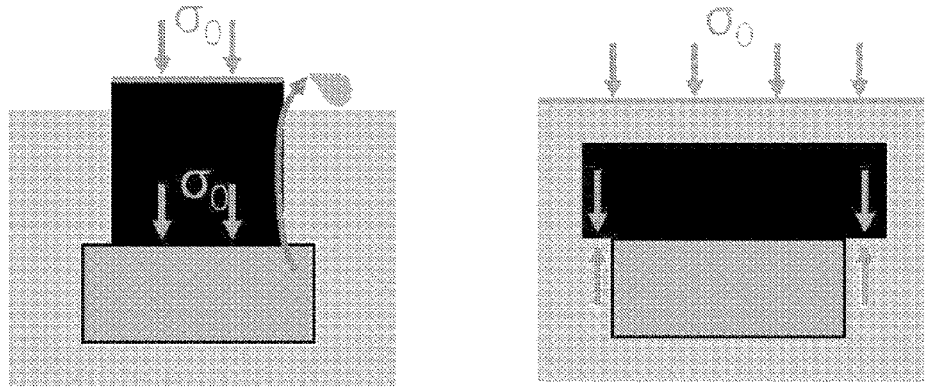
FIGS. 12A-12C illustrate an experiment result of a resistance change with respect to a pressure according to various values of $k_t$.
Figure 12:
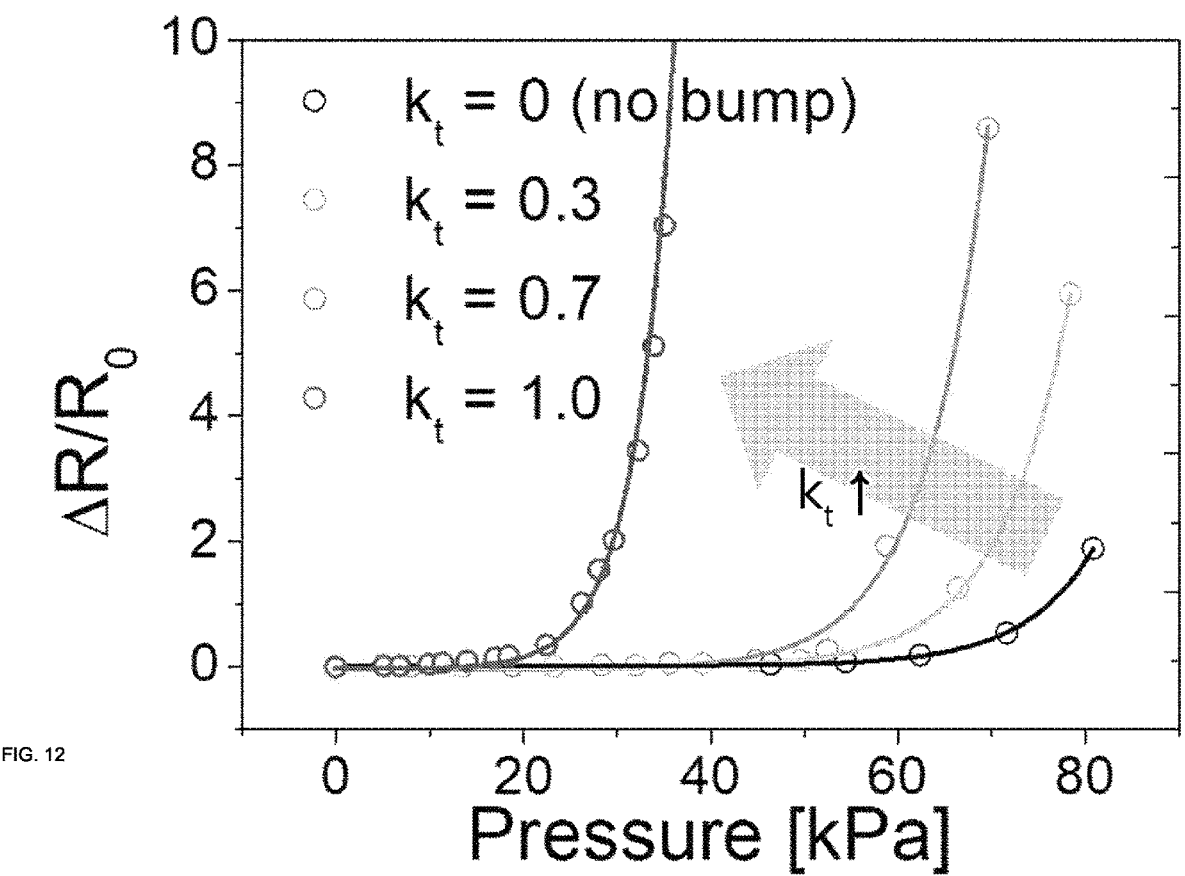

FIGS. 12A-12C illustrates an experiment result of a resistance change with respect to a pressure according to various values of $k_t$, and it may be appreciated that as the value of $k_t$ is increased, the sensitivity is drastically increased, as compared with a case in which $k_t=0$ (that is, a case in which no microbump is present). For example, in a case in which the flexible pressure sensor 100 needs to measure a very weak signal like a pulse, or in a case in which the flexible pressure sensor 100 needs to have a very small size, it is much more advantageous for the flexible pressure sensor 100 to have the exposed bump structure as illustrated in FIG. 11B.

Figure 13:
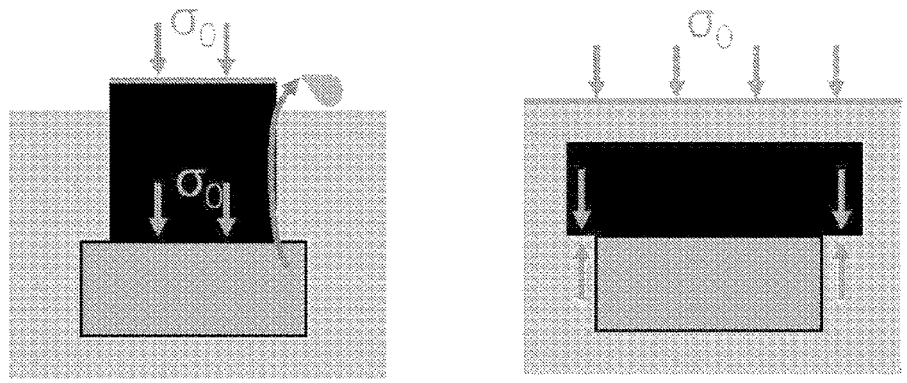
FIGS. 13A-13C illustrates an experiment result of a resistance change with respect to a pressure according to various values of $k_w$.
Figure 13:
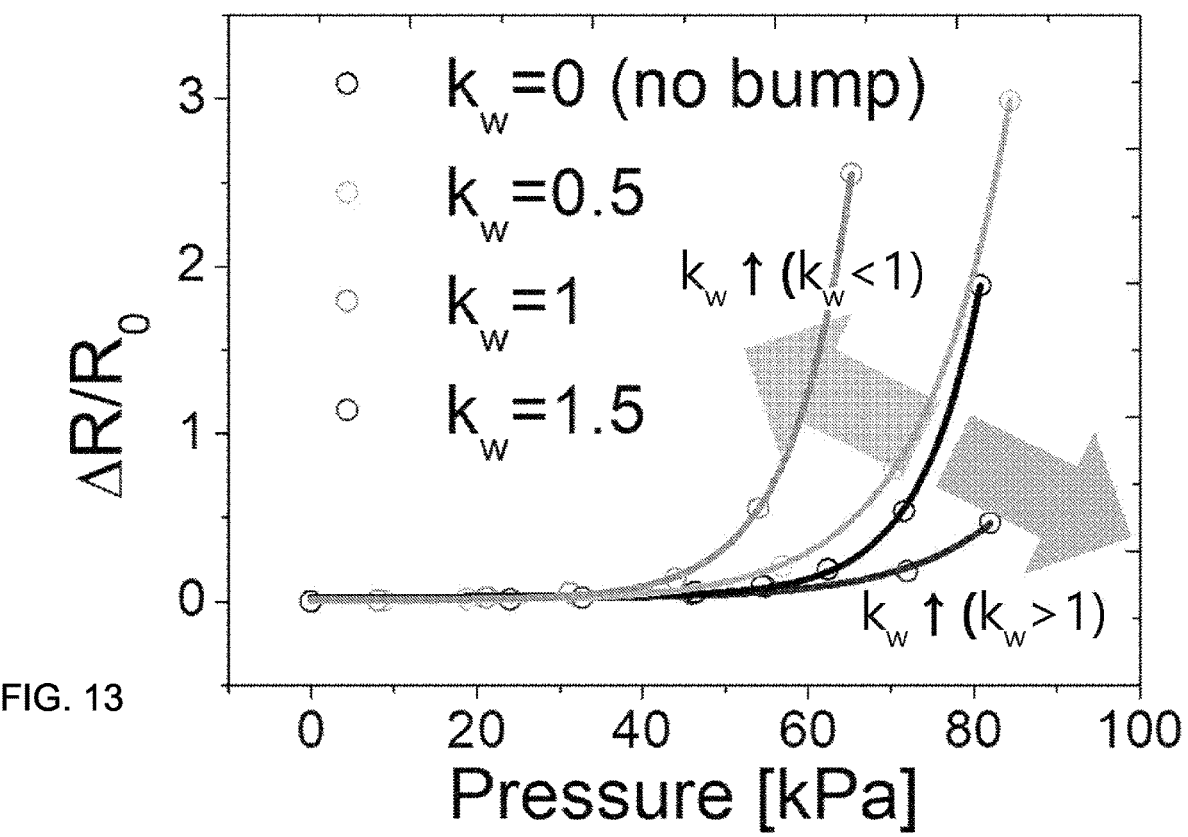

FIGS. 13A-13C illustrate an experiment result of a resistance change with respect to a pressure according to various values of $k_w$. In a case in which the value of $k_w$ is smaller than 1 (that is, the width of the microbump<the width of the microchannel, $k_w<1$), as the value of $k_w$ is increased, the sensitivity is increased (in the same context as the experiment result of FIG. 8 described above), as compared with a case in which $k_w=0$ (that is, a case in which no microbump is present). On the contrary, in a case in which the value of $k_w$ is larger than 1 (that is, the width of the microbump>the width of the microchannel, $k_w>1$), as the value of $k_w$ is increased, the sensitivity is decreased.

Figure 14:
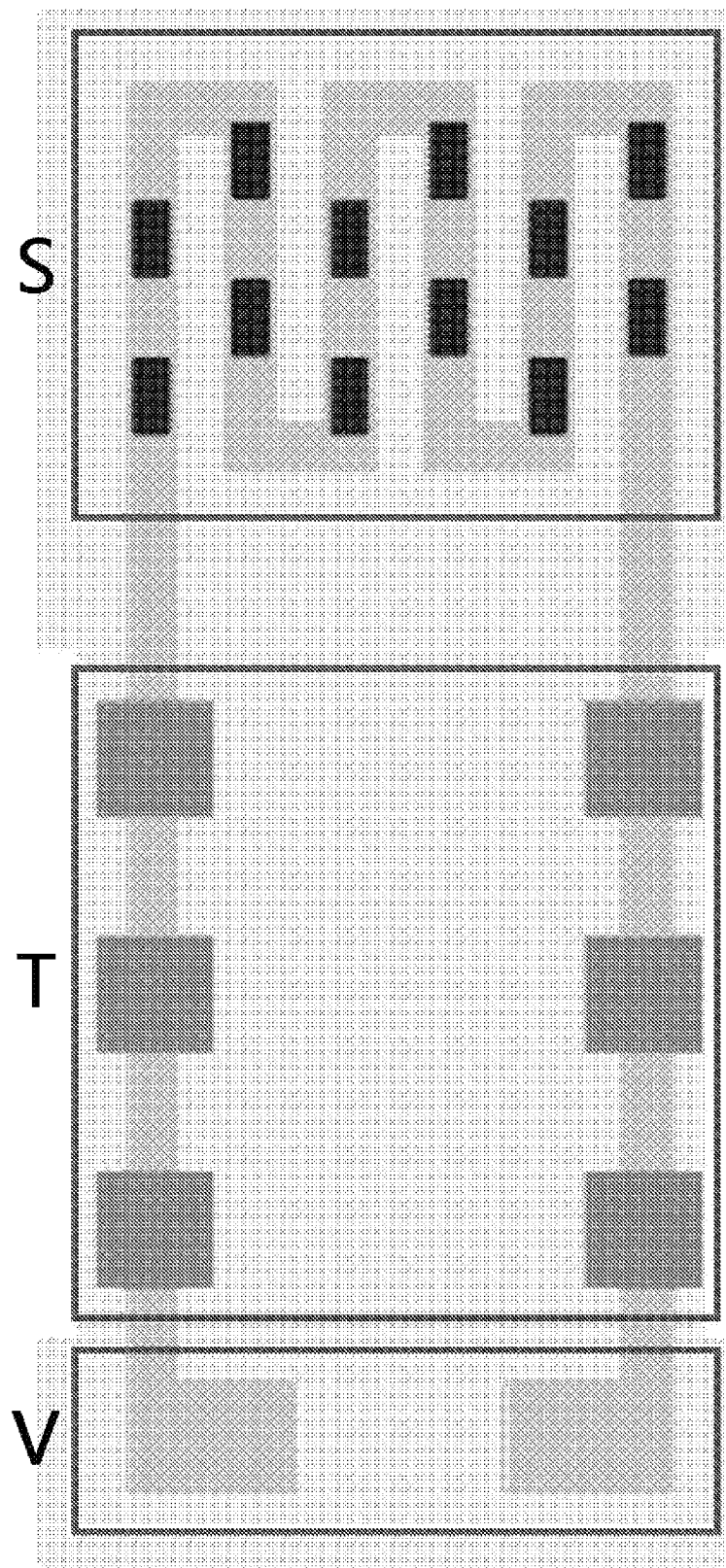
FIG. 14 illustrates an example of the flexible pressure sensor according to the present invention to which an anchored bump structure is applied.

As illustrated in FIG. 1 and the like, the flexible pressure sensor 100 includes the sensing portion S where pressure sensing is performed, and the reservoir V for transmission and reception of a signal to and from the outside, and the sensing portion S and the reservoir V are appropriately spaced apart from each other. Here, it is preferable that a portion (hereinafter, referred to as connection portion T) between the sensing portion S and the reservoir V has a structure in which a signal is not changed even when a pressure is applied (that is, the connection portion T has a low sensitivity). In this case, it is advantageous for the flexible pressure sensor 100 to have the anchored bump structure as illustrated in FIG. 11C. FIG. 14 illustrates an example of the flexible pressure sensor according to the present invention to which the anchored bump structure is applied. More specifically, FIG. 14 illustrates an example in which the anchored bump structure as illustrated in FIG. 11C is applied to the connection portion T between the sensing portion S and the reservoir V. In this case, even when an unexpected external pressure is applied to the connection portion T, since the connection portion T has a low sensitivity, it is possible to prevent an unnecessary noise in a process in which the pressure sensed at the sensing portion S is transferred to the reservoir V as much as possible.

Figure 15:
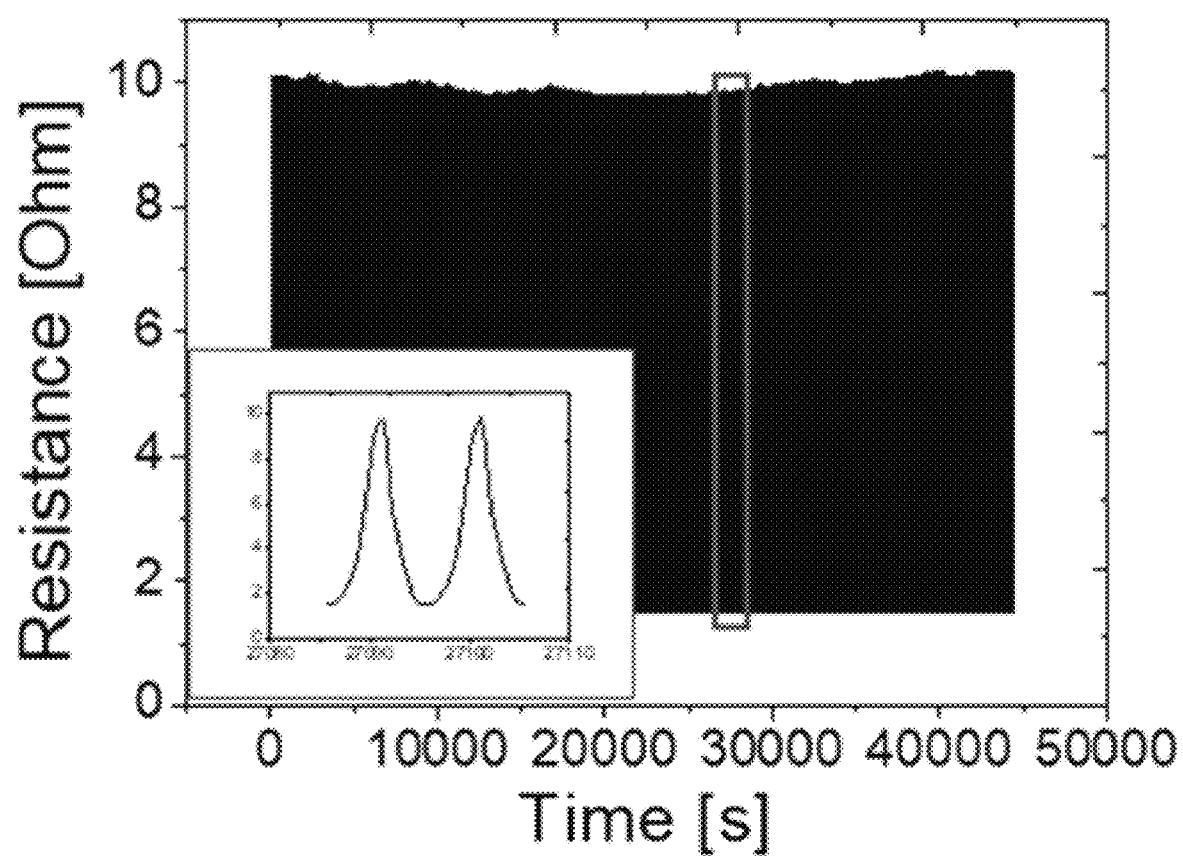
FIG. 15 illustrates an experiment result of a repetitive test.

FIG. 15 illustrates an experiment result of a repetitive test. That is, the repetitive test was performed to check whether or not the flexible pressure sensor 100 according to the present invention manufactured as described above shows a predetermined resistance change with repetitive application of a pressure. As a result, it may be seen that the flexible pressure sensor 100 showed the predetermined resistance change for 5000 times or more with respect to the constant and repetitive application of a pressure. That is, it may be seen from the result that the sensor using the conductive liquid has a high signal stability. Such a characteristic greatly affects the life span of the wearable device. The higher the signal stability, the longer the life span of the sensor becomes.

[4] Utilization Examples of Flexible Pressure Sensor According to Present Invention There are various methods of utilizing the flexible pressure sensor 100 according to the present invention manufactured as described above in health monitoring application. Hereinafter, a pulse measurement system that measures vital signs, and a body pressure distribution measurement system that measures a body motion will be described by way of example.

Figure 16A:
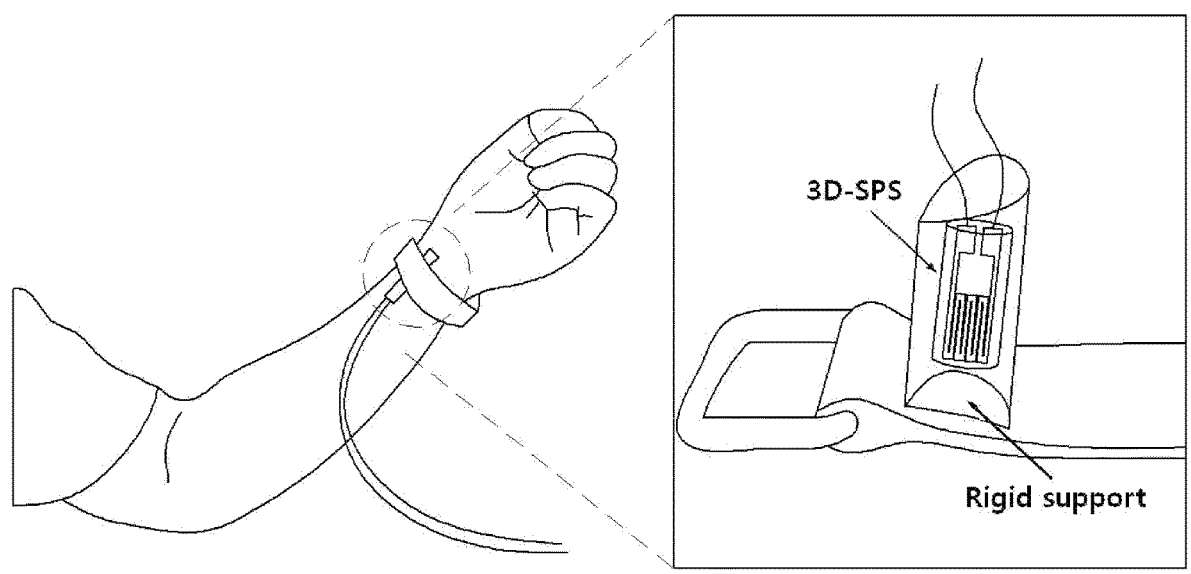
FIGS. 16A to 17 are diagrams for describing a pulse measurement system using the flexible pressure sensor according to the present invention.
Figure 16B:
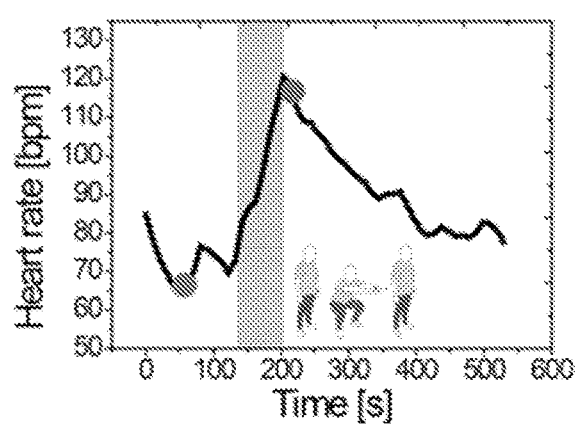
Figure 16E:
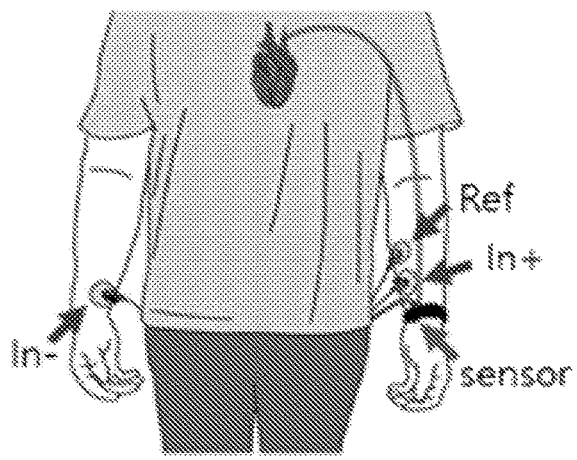
Figure 16F:
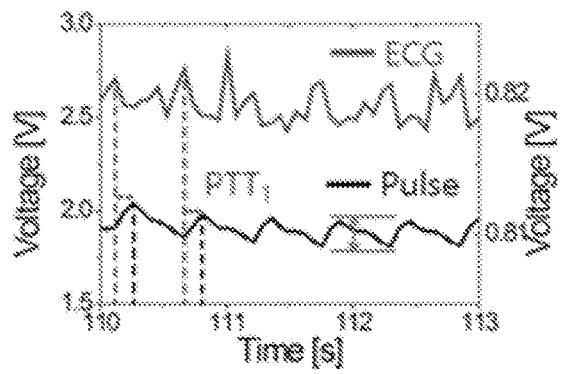
Figure 16G:
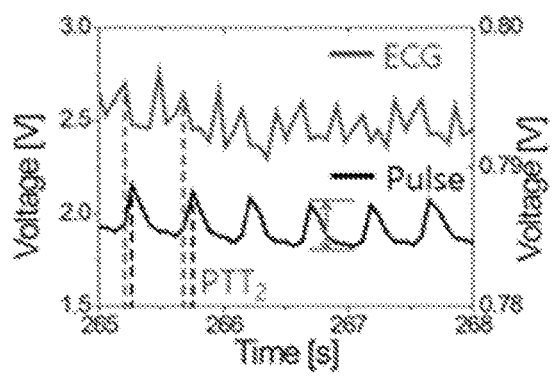
Figure 16C:
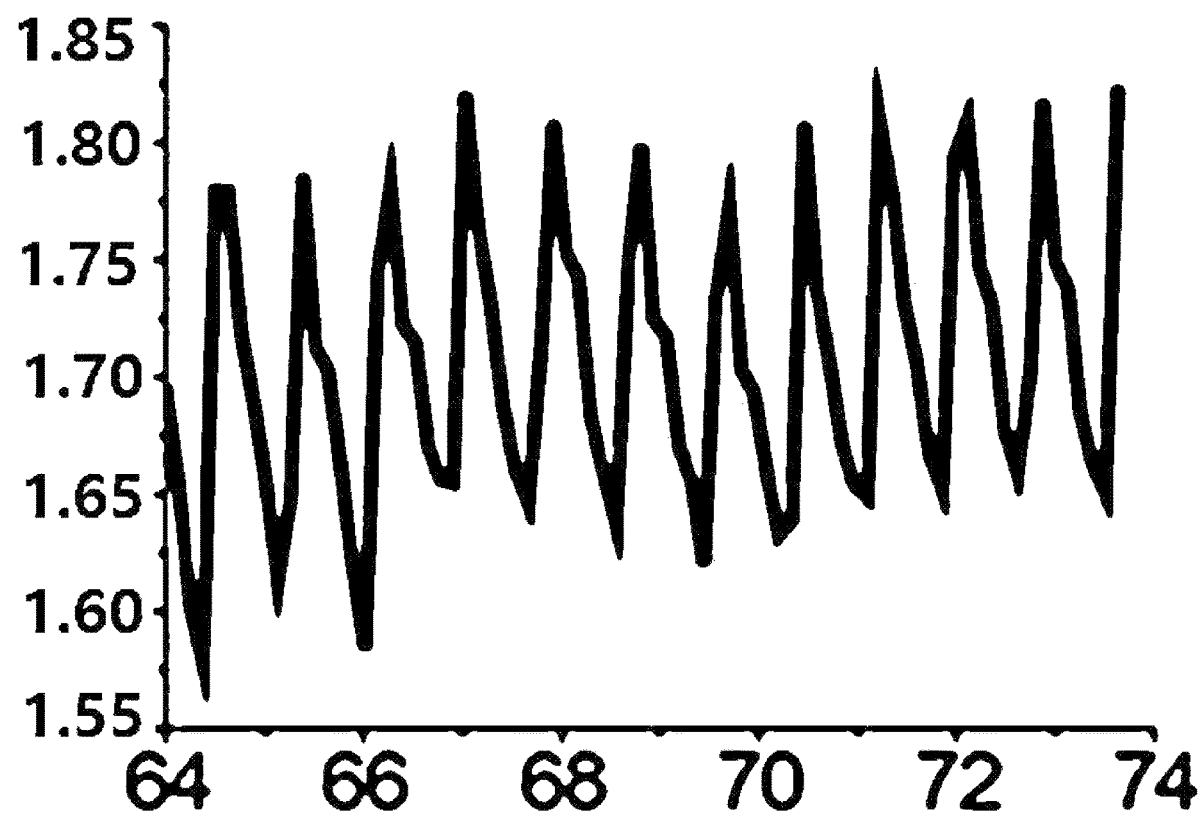
Figure 16D:
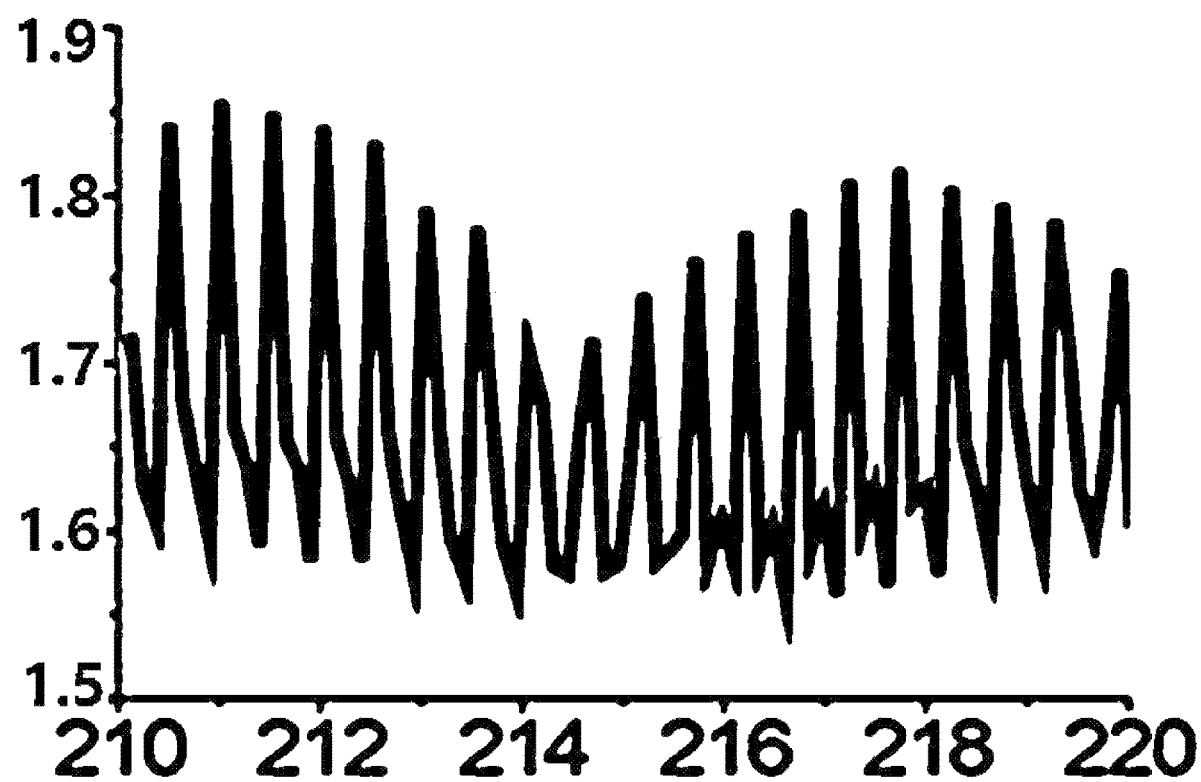
Figure 17:
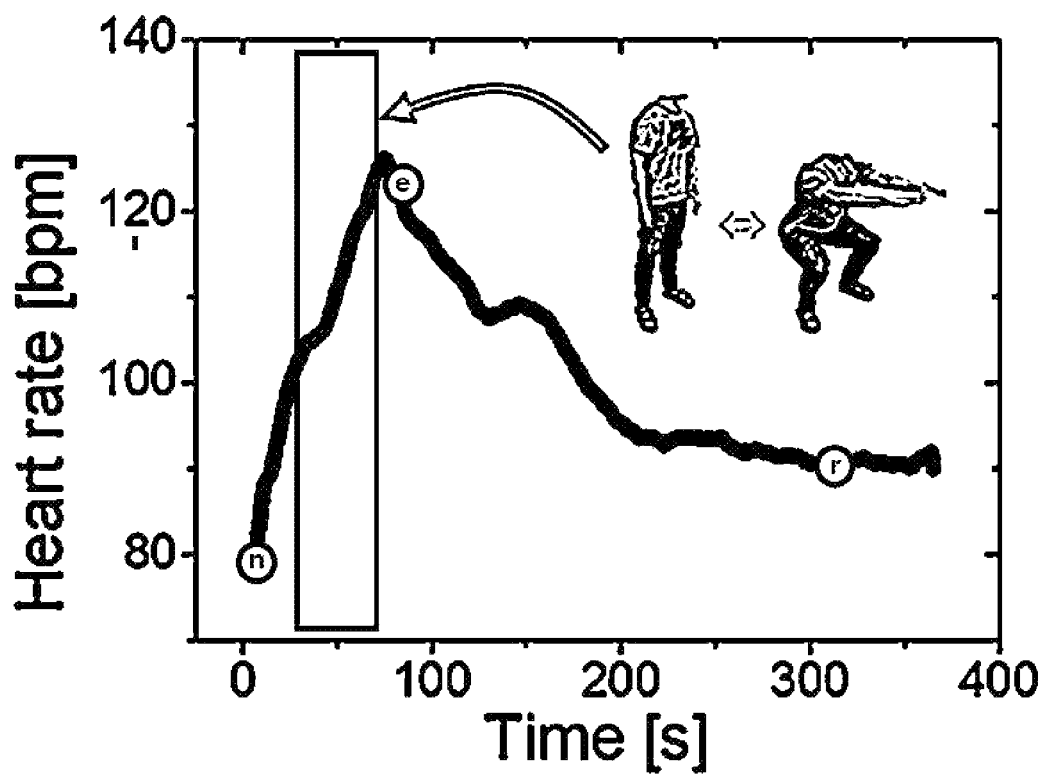
Figure 17:
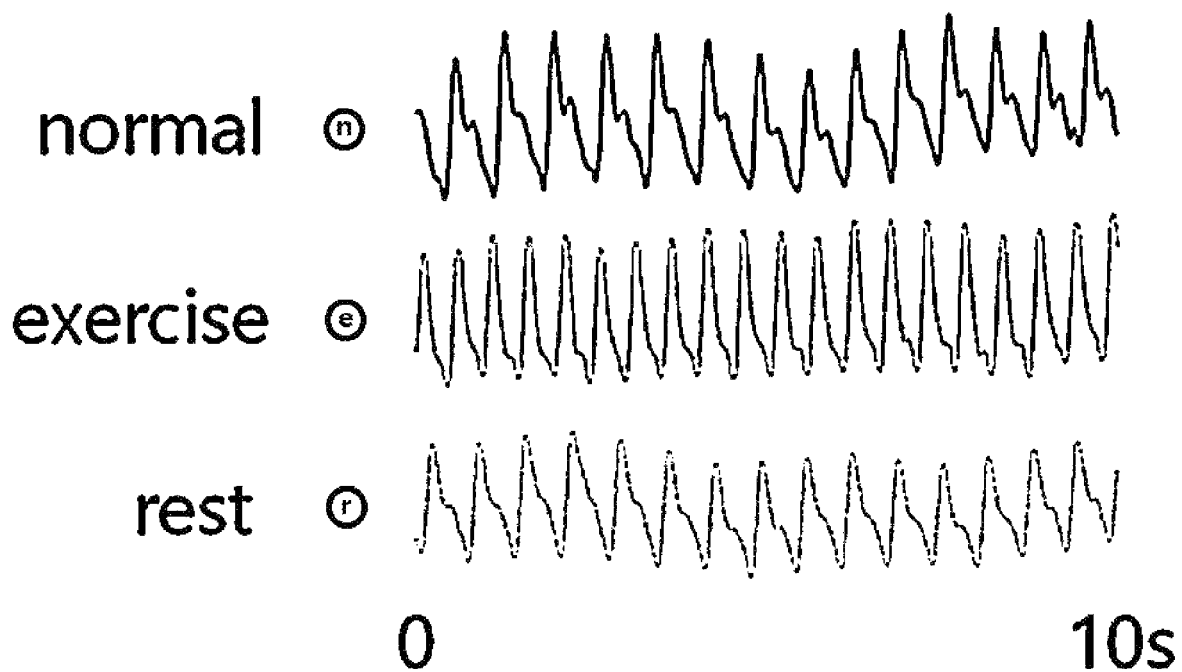

FIGS. 16A to 17 are diagrams for describing a pulse measurement system using the flexible pressure sensor according to the present invention.

A pulse is an index that most simply indicates information on a current health condition of a user in a wearable device. First, referring to FIGS. 16A to 16G, the developed flexible pressure sensor may measure a small pressure from a surface of the skin, the small pressure being transferred by constriction and dilation of blood vessels in the wrist (FIG. 16A). The intensity of the pulse transferred from the blood vessels in the wrist varies depending on a position and each person. Therefore, the size of the sensor may be changed to a size most suitable for measurement for each user. Basically, the sensor may have a pressure measurement region having a size 10×10 mm or 20×10 mm to perform the pulse measurement. Further, the pressure sensor is manufactured in a form of a bracelet that may surround the wrist, and the pulse measurement is performed.

In addition, an algorithm that may measure a blood pressure by using electrocardiogram (ECG) data (FIG. 16B). FIG. 16C is a pulse signal graph with respect to time at the lowest point (green dot) in FIG. 16B, and FIG. 16D is a pulse signal graph with respect to time at the highest point (red dot) in FIG. 16B. It may be intuitively appreciated from FIGS. 16C and 16D that a pulse rate is increased after exercise. The blood pressure is an index indicating medically more meaningful information as compared with the pulse. There have been various attempts to simply estimate the blood pressure by using various methods. As one of the attempts, various algorithms for estimating the blood pressure by using data of a pulse transit time (PTT) have been developed, the PTT being a difference between a peak point in electrocardiogram and a peak point in pulse data. FIG. 16E is an experiment overview diagram for checking a change of the PTT before and after exercise by measuring the pulse and the ECG at the same time. Here, Ref, In+, and In− indicate three electrodes required for the ECG measurement. FIGS. 16E and 16F illustrate results showing a decrease of the PTT before and after the experiment, and it may be indirectly appreciated from the result that the blood pressure increased.

FIG. 17 illustrates a result of measuring a change of the pulse depending on a degree of physical activity by using the flexible pressure sensor according to the present invention. As clearly illustrated in FIG. 17, a change of the pulse signal is clearly shown in each of a normal state, an exercise state, and a rest state, and it may be appreciated that the flexible pressure sensor according to the present invention sensitively measures the change.

In addition, as described above, it is preferable that the microbump 130 included in the flexible pressure sensor 100 has the exposed bump structure to more sensitively measure a pulse which is a weak signal, in the pulse measurement system.

FIGS. 18A to 20 are diagrams for describing a body pressure distribution measurement system using the flexible pressure sensor according to the present invention.

Measurement of body pressure distribution may be very useful as an index for estimating a posture of a patient lying on a bed or a body leaning on another object such as a chair. In particular, a stroke patient or a patient who is unable to move his/her body is highly likely to get a secondary disease such as a bedsore when lying on a bed for a long time, and thus there is a need to periodically change a posture of such a patient. In this case, it is possible to configure a system capable of simply notifying a carer or a nurse of an uncomfortable body part or a fact that a certain pressure is applied to one body part for a certain time, which may be noticed by no one other than the patient, by mainly monitoring body pressure distribution around a body part that is likely to get a bedsore.

Figure 18A:
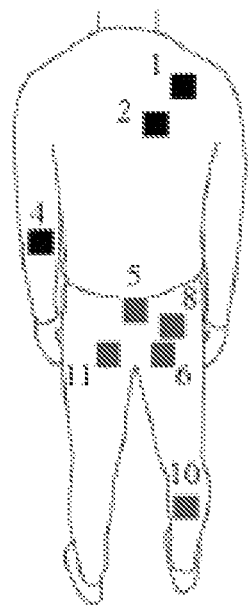
FIGS. 18A to 20 are diagrams for describing a body pressure distribution measurement system using the flexible pressure sensor according to the present invention.
Figure 18B:
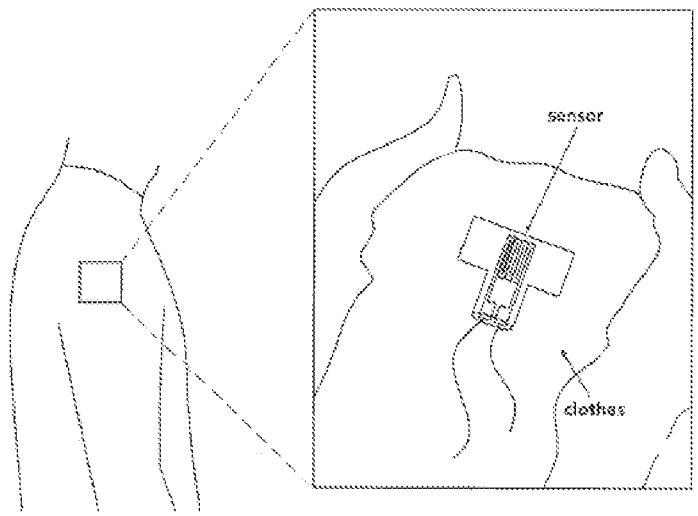
Figure 18C:
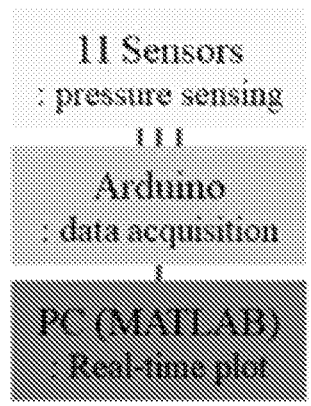
Figure 18D:
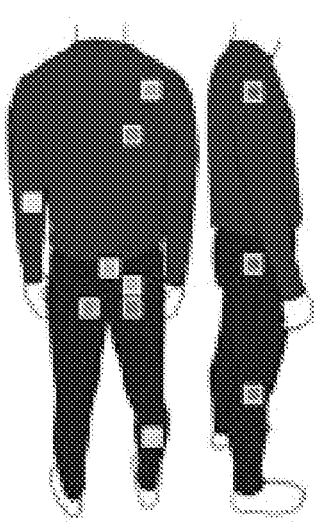
Figure 18E:
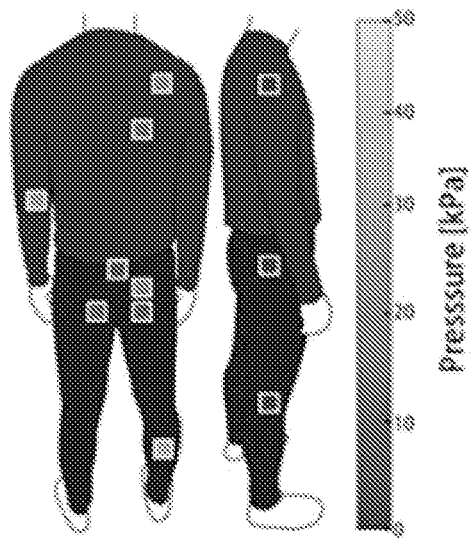

Examples of the body part that is likely to get a bedsore include bony areas such as shoulders, wing bones, elbows, knees, and a tailbone. Representative parts are selected and multiple pressure sensors are attached to clothes in array (FIG. 18A). The attached flexible pressure sensor is firmly attached to fibers of the clothes and thus is not easily detached (FIG. 18B). A circuit is implemented using Arduino to collect data transferred from the multiple pressure sensors (FIG. 18C), and a system in which real-time monitoring may be performed by a personal computer (PC) through the circuit may be developed (FIG. 18D).

Figure 19:
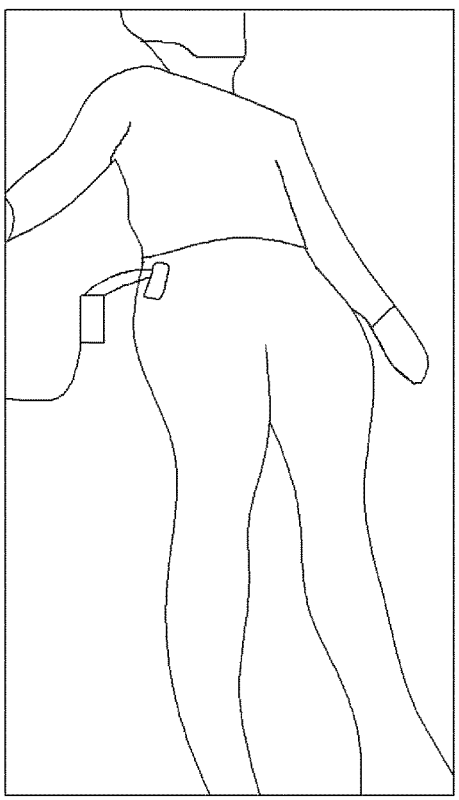
Figure 19:
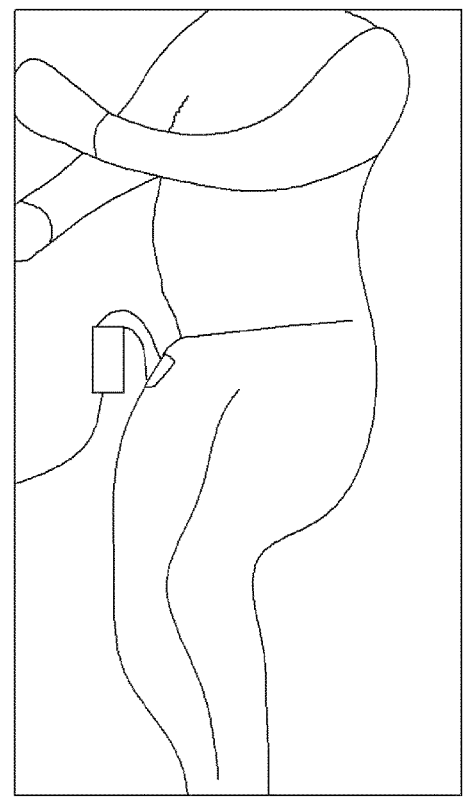
Figure 19B:
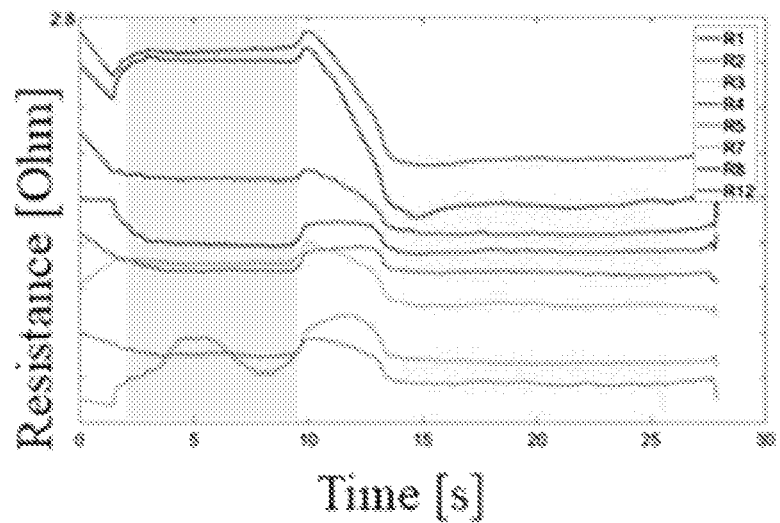
Figure 19C:
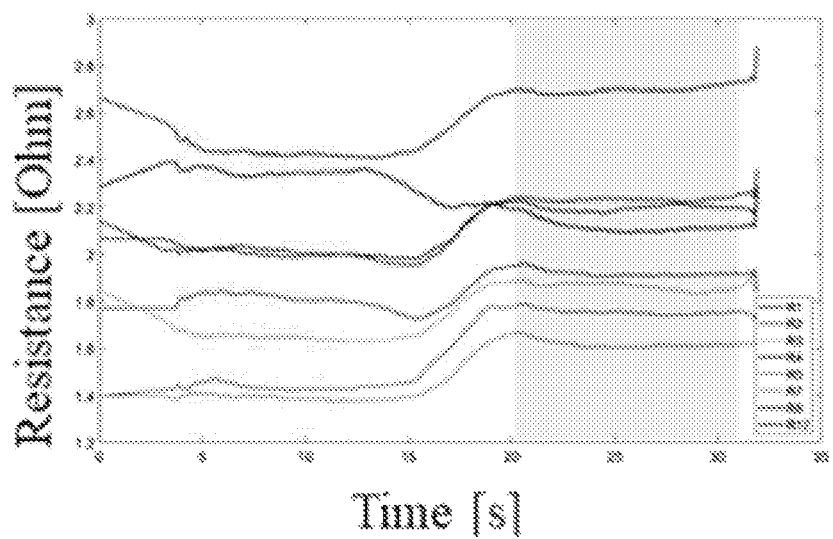

In an experiment actually performed using the developed system, a change of a signal caused by a change from a state of lying on the back on a bed (FIG. 19A1) to a state of lying on the side on the bed (FIG. 19A2) or a change from the state of lying on the side on the bed to the state of lying on the back on the bed was checked. In a case illustrated in FIG. 19A1, the entire body is in contact with the bed, and thus a pressure was transferred to the sensor as it is. However, in a case of the change to the state of FIG. 19A2, no pressure is applied to a sensor positioned on the back of the body, and only a sensor positioned on the side of the body senses a pressure (FIG. 19B). On the contrary, in a case of the change from the state of FIG. 19A2 to the state of FIG. 19A1, it may be seen that a signal value of the sensor positioned on the side of the body is decreased, and a signal value of the sensor positioned on the back of the body is increased (FIG. 19C). As a result, it may be appreciated that the pressure sensor array system attached to the clothes may be utilized to grasp and monitor the body motion.

Figure 20:
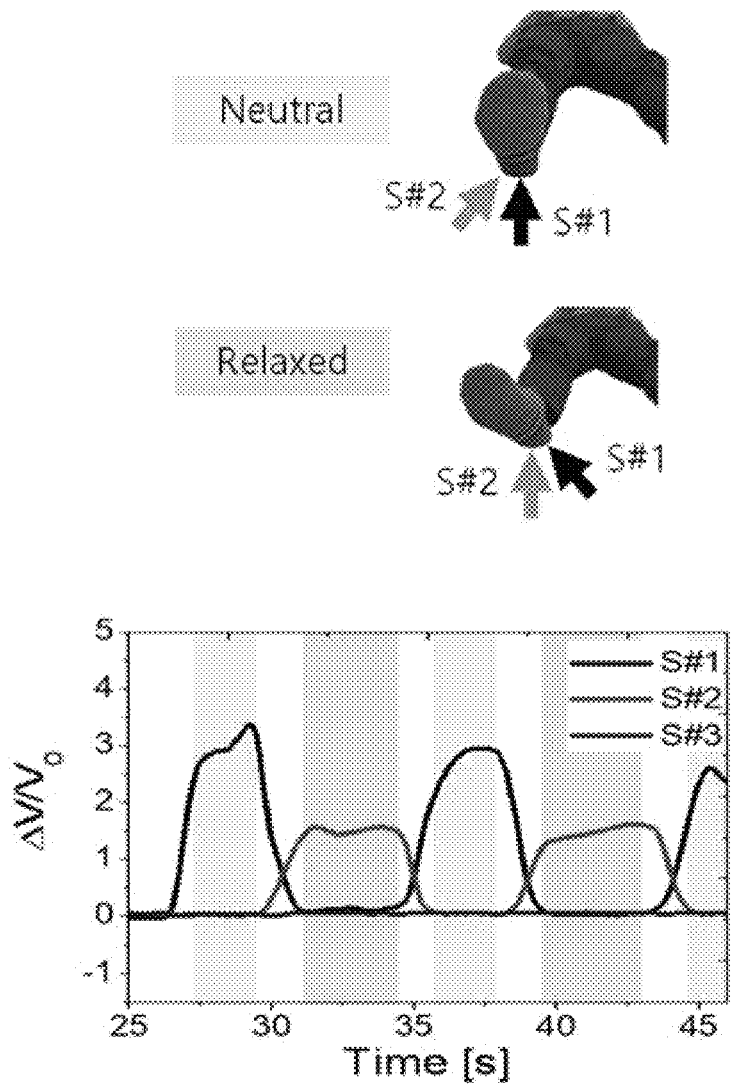
Figure 20:
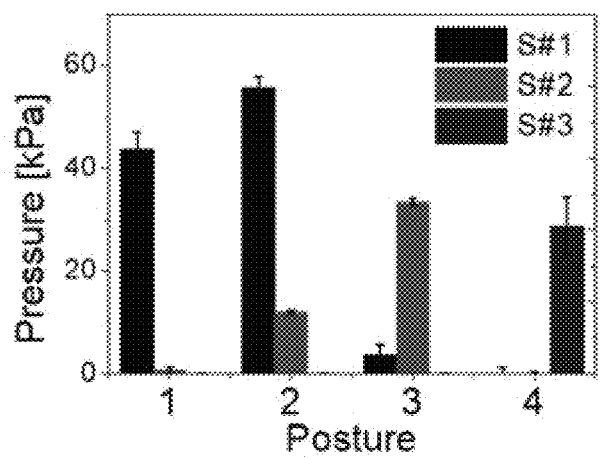
Figure 21:
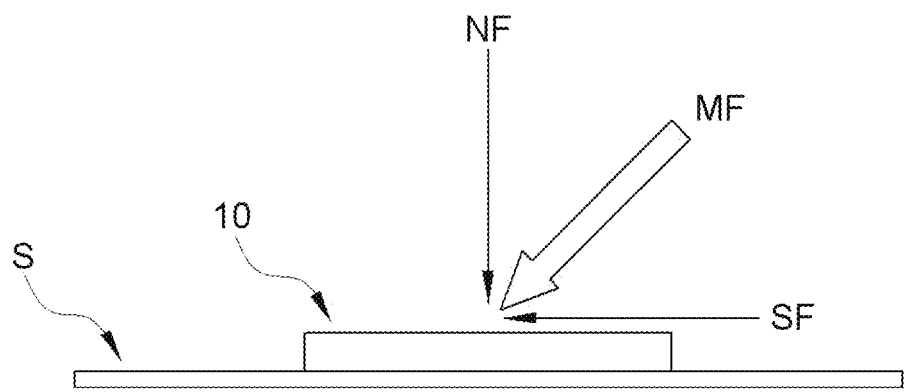
FIG. 21 is a diagram illustrating a multi-directional force applied to a general pressure sensor.
Figure 22A:
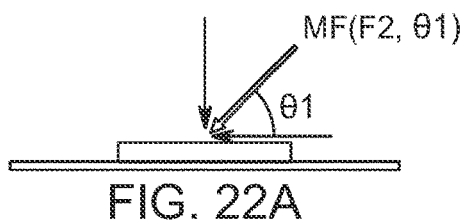
FIGS. 22A-22F are diagrams illustrating resistance changes sensed depending on a magnitude and direction of a force applied to the general pressure sensor.
Figure 22B:
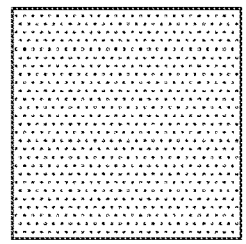
Figure 22C:
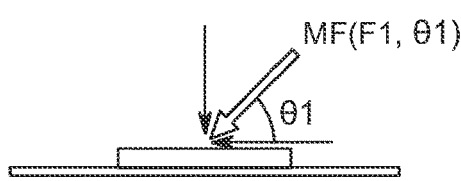
Figure 22D:
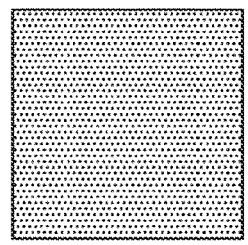
Figure 22E:
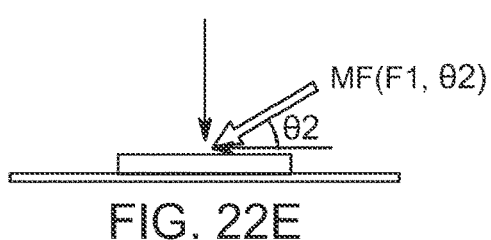
Figure 22F:
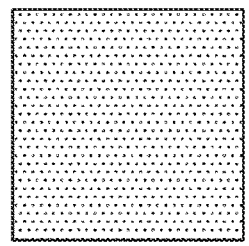

FIG. 20 illustrates an example in which the flexible pressure sensor according to the present invention is attached to a heel and a heel pressure is monitored. In a case in which sensors are attached at intervals to a heel as illustrated in drawings on the upper side of FIG. 20, a larger pressure is applied to a sensor S #1 attached to the center of the heel when in a neutral state in which a user sits with legs straight out in a slight tension state, and a larger pressure is applied to a sensor S #2 attached to the outer side of the heel when in a relaxed state in which the user is in a completely relaxed state. A drawing on the middle side of FIG. 20 illustrates a pressure signal (converted into a voltage V) measured with respect to time in the neutral/relaxed state, a drawing on the lower side of FIG. 20 illustrates a pressure change depending on a posture, and it may be appreciated that the measurement of a heel pressure may be very smoothly performed.

[5] Multi-Directional Physical Sensor According to Present Invention

Figure 23:
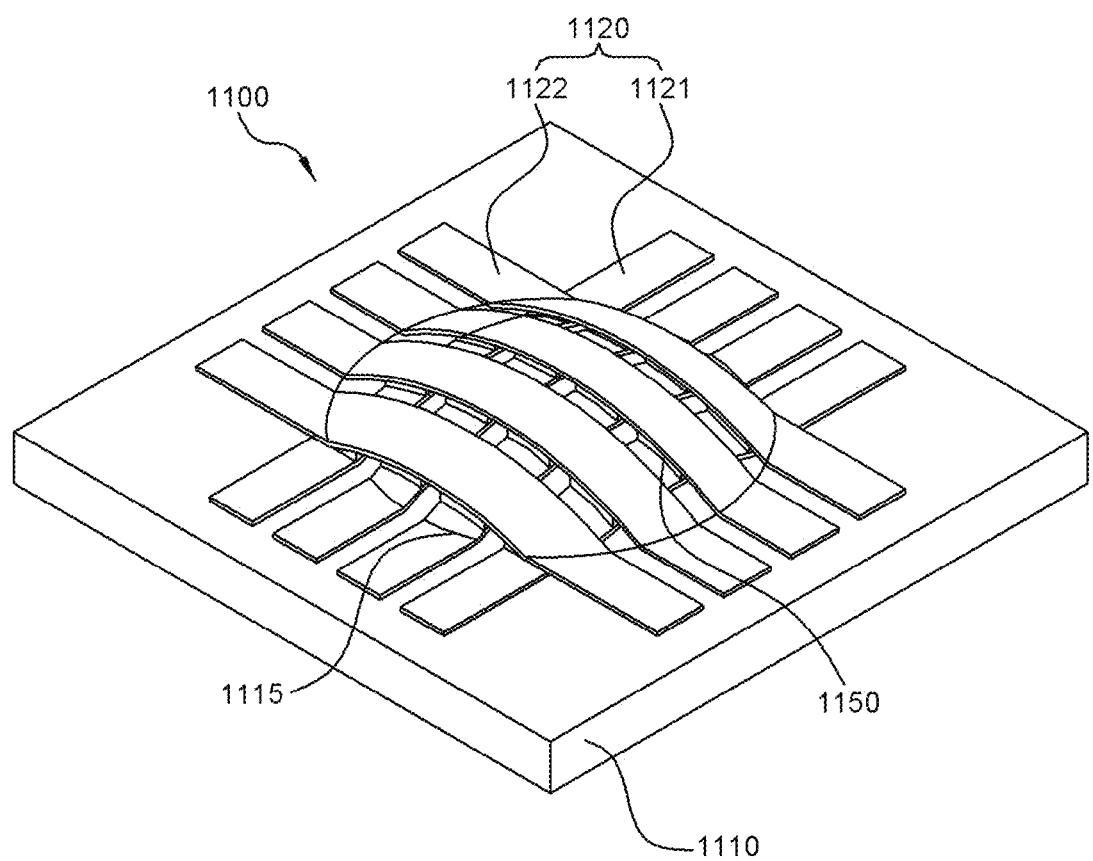
FIG. 23 is a perspective view illustrating a multi-layer microchannel array of a multi-directional physical sensor according to an embodiment of the present invention.
Figure 24:
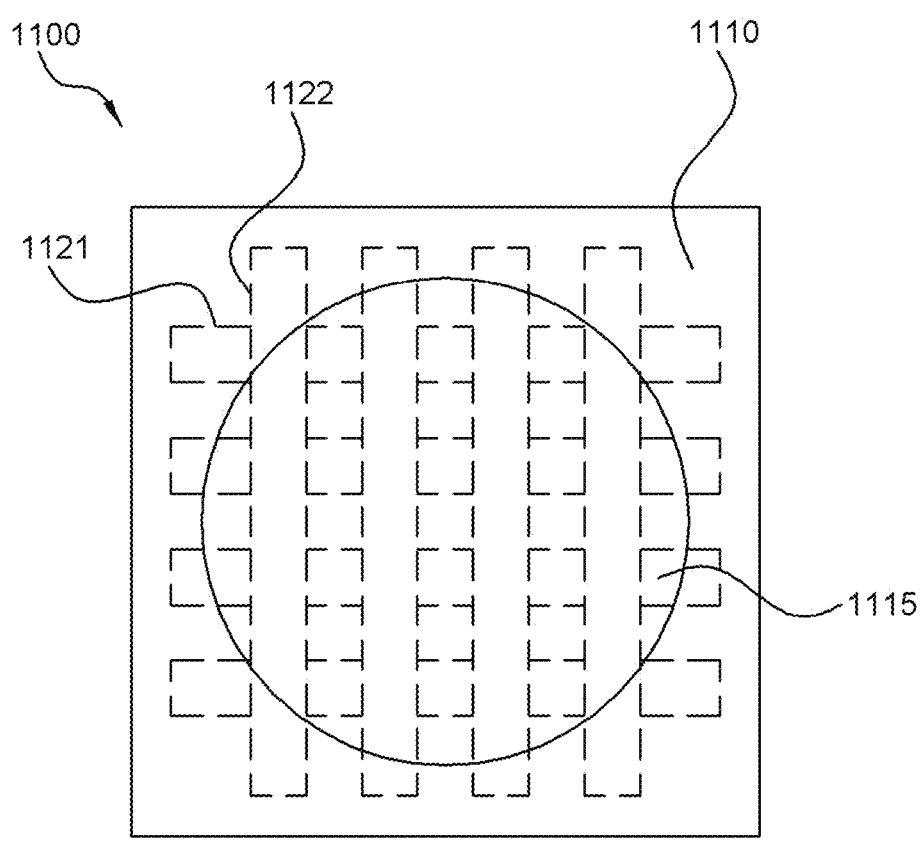
FIG. 24 is a plan view illustrating the multi-layer microchannel array of the multi-directional physical sensor according to an embodiment of the present invention.
Figure 25:
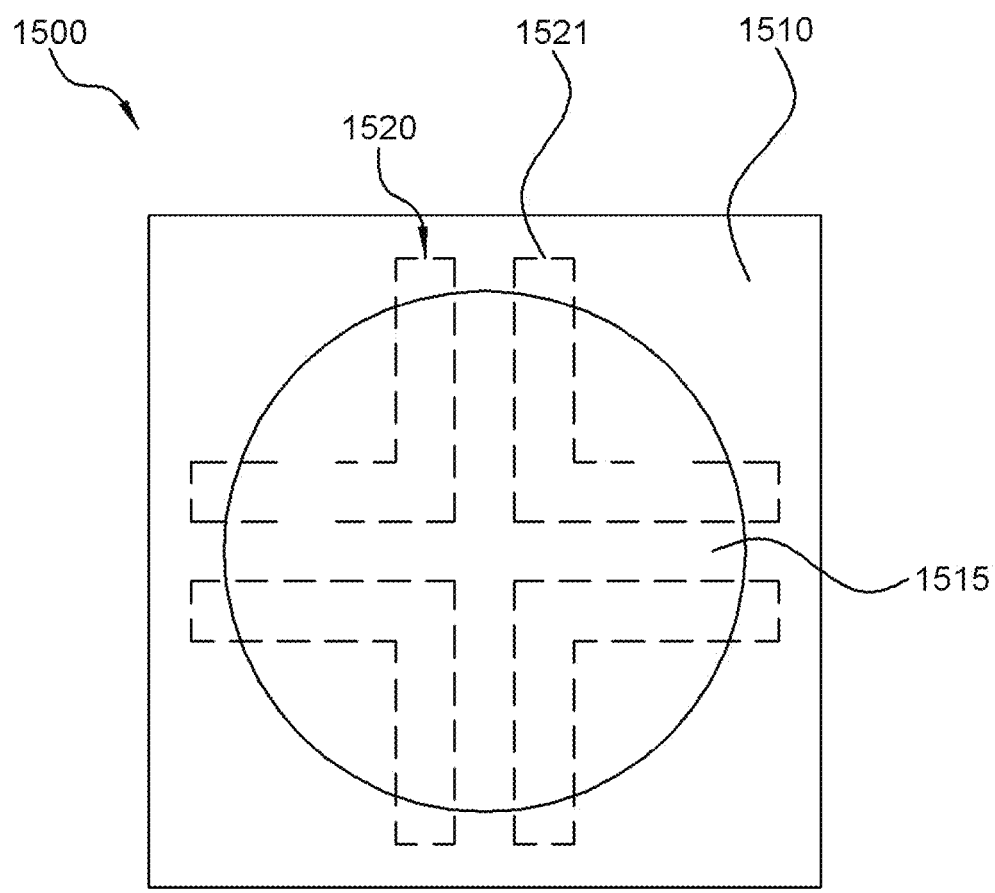
FIG. 25 is a plan view illustrating a multi-layer microchannel array of a multi-directional physical sensor according to another embodiment of the present invention.

FIG. 23 is an overall perspective view of a multi-directional physical sensor 1100 according to an embodiment of the present invention, and FIG. 24 is a plan view of the multi-directional physical sensor 1100. Further, FIG. 25 is a plan view of a multi-directional physical sensor 1500 according to another embodiment of the present invention.

As illustrated in FIG. 23, the multi-directional physical sensor 1100 includes: a flexible body 1110 including a protruding portion 1115 having a three-dimensionally and externally protruding shape, for example, a dome shape; a microchannel 1120 coupled to or embedded in the flexible body 1110 on the upper side of the flexible body 1110; and a bump 1150 provided between channels stacked in multiple layers in the microchannel 1120.

The flexible body 1110 is formed of a flexible material to be applicable to a wearable device. The flexible body 1110 is formed of an elastomer having a high flexibility to smoothly cope with various deformations such as stretching, folding, and twisting. The flexible body 1110 supports the microchannel 1120. Specifically, the flexible body 1110 is formed of a material having a Young's modulus of 1 GPa or less, and an elongation ratio may be 20 to 1000%.

Here, the flexible body 1110 may have a three-dimensionally protruding shape including the protruding portion 1150 that protrudes upward so that the center protrudes the most, such that the supported microchannel 1120 may sense a shear force. In a case where the microchannel 1120 is disposed on a plane, a normal force may be easily sensed, but the shear force may not be sensed or accuracy of the sensing of the shear force significantly deteriorates. Therefore, the flexible body 1110 according to the present invention includes the protruding portion 1150, and the microchannel 1120 is formed to have a shape corresponding to a protruding shape of the protruding portion 1150 and is coupled to or embedded in the upper side of the protruding portion 1150, such that it is easy to sense a shear force applied to the sensor.

The protruding portion 1150 may protrude in a three-dimensional shape such as a circular shape, an oval shape, or a square shape. FIG. 23 illustrates a case where the microchannel 1120 is coupled to the upper side of the flexible body 1110. However, the microchannel 1120 may also be embedded in the flexible body 1110 so that the flexible body 1110 is also formed on the upper side of the microchannel 1120 (see FIG. 26).

Referring to FIG. 24, the microchannel 1120 includes a plurality of first channels 1121 which extend in a horizontal direction and are arranged while being spaced apart from each other in a vertical direction, and a plurality of second channels 1122 which are disposed on the first channels 1121, extend in the vertical direction, and are arranged while being spaced apart from each other in the horizontal direction. That is, the first channels 1121 and the second channels 1122 may be arranged while intersecting each other in a lattice form. The microchannel 1120 may be formed of a conductive liquid material to implement the flexible measurement sensor 1100. Preferably, the microchannel 1120 may be formed of a liquid metal to improve convenience in manufacturing and to significantly reduce an influence of an external conductor. The liquid metal may drive the sensor with low power due to high conductivity, and is highly adaptive to various physical deformations and thus does not lose electrical properties, which is advantageous. Therefore, the sensor 1100 manufactured in a form in which the liquid metal fills the microchannel 1120 in the flexible body 1110 formed of the elastomer is highly suitable as a wearable sensor, because a performance difference such as a change in basic resistance does not occur even in a case of various physical deformations such as stretching, folding, and twisting. As the liquid metal, mercury or galinstan may be used. More preferably, galinstan which is non-toxic to humans may be used. Galinstan is an alloy of gallium, indium, and tin, and is present in a liquid state at room temperature. A cross-sectional area of such a microchannel 1120 is changed (decreased) when a pressure is applied, and a resistance is changed due to the change. Therefore, an external force applied to the sensor 1100 is measured by converting the change in resistance into a pressure or force.

Therefore, in a case where a multi-directional force is applied at a predetermined angle along a vertical direction in the drawing, both a magnitude and a direction of the force may be sensed through a change in resistance sensed in each of the plurality of first channels 1121, and in a case where a multi-directional force is applied at a predetermined angle along a horizontal direction in the drawing, both a magnitude and a direction of the force may be sensed through a change in resistance sensed in each of the plurality of second channels 1122. That is, according to the present invention, it is possible to sense a magnitude and direction of a multi-directional force applied in a three-dimensional direction through the microchannel 1120. In the drawing, the microchannel 1120 includes two layers. However, additional channels may further be stacked to improve accuracy in direction sensing, the additional channels being arranged in a row along the plane so as not to be parallel to the first and second channels 1121 and 1122. That is, the multi-directional physical sensor 1100 includes a plurality of additional unit channels disposed on the second channels 1122, having a predetermined length, and arranged while being spaced apart from each other at a predetermined interval along the plane. The additional unit channels are disposed in a state of being inclined with respect to first unit channels constituting the first channels 1121 and second unit channels constituting the second channels 1122 at a predetermined angle or more, respectively.

According to an additional embodiment, a microchannel 1520 may include a single layer as illustrated in FIG. 25. That is, a multi-directional physical sensor 1500 according to another embodiment of the present invention includes: a flexible body 1510 including a protruding portion 1515 having a three-dimensionally and externally protruding shape, for example, a dome shape; and a microchannel 1520 coupled to the upper side of the flexible body 1510. In this case, the microchannel 1520 includes a plurality of unit channels 1521. However, the respective unit channels 1521 are arranged while being spaced apart from each other so as not to intersect each other, and each unit channel may be bent so that opposite ends face two different directions, respectively. As such a plurality of unit channels 1521 enable sensing of a direction (two directions) of a force, it is possible to sense both a magnitude and a direction of a multi-directional force. In addition, it is possible to improve sensitivity with respect to a direction of a force by increasing the number of unit channels 1521 or decreasing an angle formed by opposite ends of each unit channel.

Meanwhile, in the multi-directional physical sensor 1100, the bump 1150 may be provided at a portion where the first channel 1121 and the second channel 1122 intersect each other to minutely transfer the external force to the first channel 1121 disposed to face the inner side of the second channel 1122. The bump 1150 is formed of a hard material with a hardness higher than that of the material of the microchannel 1120, such that an external force applied to the second channel 1122 may be minutely transferred to the first channel 1121. The hard material refers to a material that is solid. The hard material is not deformed even when an external pressure is applied, unlike the flexible body 1110 that is formed of a flexible material and deformed when the external pressure is applied. Therefore, the bump 1150 may maximize a change in cross-sectional area of the first channel 1121 when a pressure is applied to the flexible body 1110.

A general channel-based pressure sensor has a low pressure sensitivity, which is disadvantageous. For use in various wearable devices, it is significantly important to have an excellent pressure sensitivity and a low limit of detection in a low pressure range of 50 kPa or less. Therefore, a structure, in which the bump 1150 is inserted as an essential element to implement a high pressure sensitivity and a wide measurement range while maintaining stable mechanical characteristics and signal stability of the liquid-metal-based pressure sensor, is applied.

Hereinafter, a detailed configuration of the multi-directional physical sensor 1100 having the configuration as described above will be described in more detail with reference to the drawing.

Figure 26:
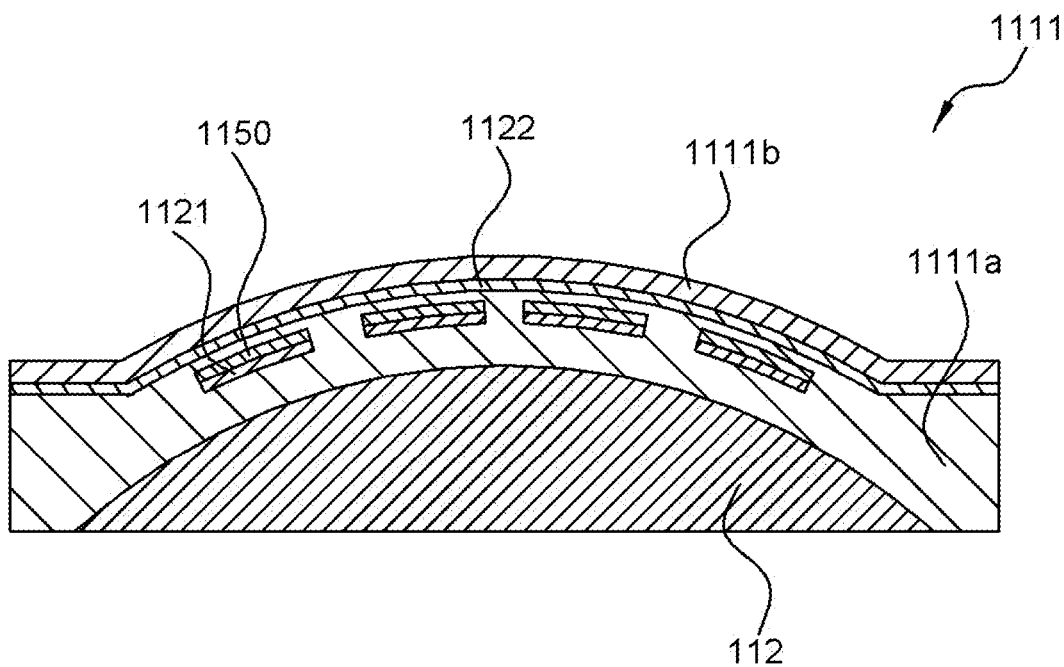
FIG. 26 is a cross-sectional view of the multi-directional physical sensor according to an embodiment of the present invention.

FIG. 26 is a cross-sectional view of the multi-directional physical sensor 1100 according to an embodiment of the present invention. As illustrated in FIG. 26, the multi-directional physical sensor 1100 includes: the flexible body 1110 including the protruding portion 1150 (see FIGS. 23 and 24) having a three-dimensional shape; the microchannel (1121 and 1122) embedded in the flexible body 1110; and the bump 1150 provided at an intersecting portion between the first channel 1121 and the second channel 1122.

The flexible body 1110 may include a first body 1111a and a second body 1111b. The first body 1111a is formed at a lower side of the microchannel (1121 and 1122) and supports the microchannel (1121 and 1122) so that the microchannel (1121 and 1122) maintains the dome shape, and the second body 1111b covers the upper side of the microchannel (1121 and 1122) to embed the microchannel (1121 and 1122) in the flexible body 1110. Further, the flexible body 1110 may include a filling material 1112 for filling a concave portion formed on the inner side of the first body 1111a due to an outward convex shape of the first body 1111a. The filling material 1112 enables the first body 1111a to maintain the dome shape. The filling material 1112 may be formed of the same material as the first and second bodies 1111a and 1111b, or may be formed of a different material with a hardness higher or lower than that of the first and second bodies 1111a and 1111b. In a case where the filling material 1112 has a hardness higher than that of the first and second bodies 1111a and 1111b, sensitivity of the sensor 1100 with respect to the external pressure is improved, and in a case where the filling material 1112 has a hardness lower than that of the first and second bodies 1111a and 1111b, a buffering capacity of the sensor 1100 is improved, such that discomfort feeling caused by an external force at the time of attachment to the body is decreased. Therefore, the material of the filling material 1112 may be selectively applied according to a use for the sensor. In other words, the filling material 1112 may serve as a support in a case of having a high hardness, or may serve as a buffer material in a case of having a low hardness.

The microchannel (1121 and 1122) is provided between the first body 1111a and the second body 1111b. The first channel 1121 and the second channel 1122 may be stacked in multiple layers in an up-down direction, and may be stacked while being misaligned with each other at a predetermined angle or more so as not to be parallel to each other. Preferably, the first channel 1121 and the second channel 1122 may be arranged to be perpendicular to each other. The first channel 1121 and the second channel 1122 may be spaced apart from each other in the up-down direction.

The bump 1150 is disposed at a portion where the first channel 1121 and the second channel 1122 intersect each other, and minutely transfer an external pressure applied to the second channel 1122 to the first channel 1121. The bump 1150 may be in contact with the first channel 1121 as illustrated in FIG. 26, or, although not illustrated, may be in contact with the second channel 1122. Alternatively, the bump 1150 may be spaced apart from both of the first channel 1121 and the second channel 1122.

As another example, a plurality of bumps 1150 each having a predetermined length may be arranged on the first channel 1121 along the first channel 1121, and spaced apart from each other at a predetermined interval.

FIGS. 27A-27C, 28A-28C and 29A-29C are diagrams illustrating resistance changes sensed depending on a magnitude and direction of a force applied to the multi-directional physical sensor 1100 according to an embodiment of the present invention.

As illustrated in FIGS. 27A-27C, 28A-28C and 29A-29C, multi-directional forces (MF) having various magnitudes F1 and F2 and various directions ($\theta 1$ and $\theta 2$) may be applied to the multi-directional physical sensor 1100. FIGS. 27A-27C, 28A-28C and 29A-29C illustrate resistance changes of first unit channels 1121a to 1121d each corresponding to a row in the first channel 1121 and second unit channels 1122a to 1122d each corresponding to a row in the second channel 1122 depending on the multi-directional force (MF).

Figure 27A:
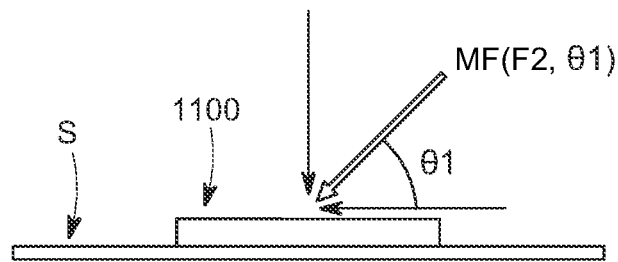
FIGS. 27A-27C, 28A-28C and 29A-29C are diagrams illustrating resistance changes sensed depending on a magnitude and direction of a force applied to the multi-directional physical sensor according to an embodiment of the present invention.
Figure 27B:
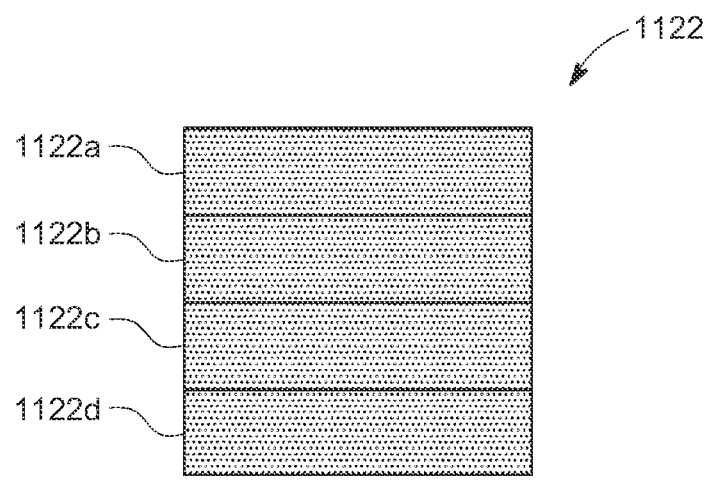
Figure 27C:
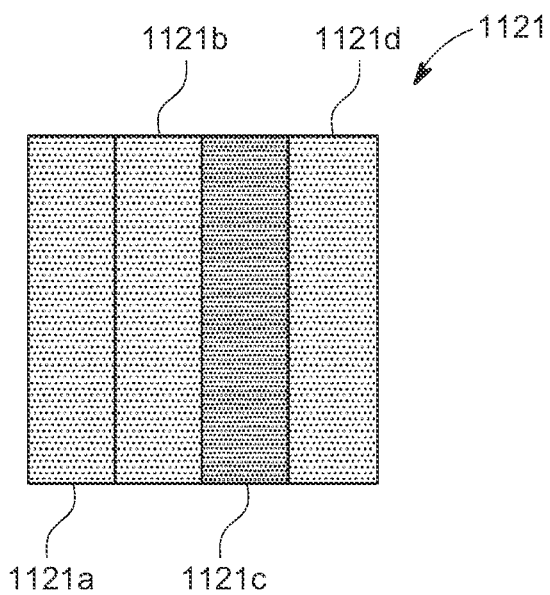

As illustrated in FIGS. 27A-27C, in a case where the multi-directional force (MF) having a second magnitude (F2) is applied in a first direction ($\theta 1$), resistance changes of the second unit channels 1122a to 1122d arranged in parallel to the first direction ($\theta 1$) based on a shear axis are the same, and a change of a resistance signal of the first unit channel 1121c that is almost perpendicular to the first direction ($\theta 1$) is largest among the first unit channels 1121a to 1121d arranged at a predetermined angle with respect to the first direction ($\theta 1$) based on the shear axis. Therefore, it is possible to infer a direction in which the multi-directional force (MF) is applied.

Figure 28A:
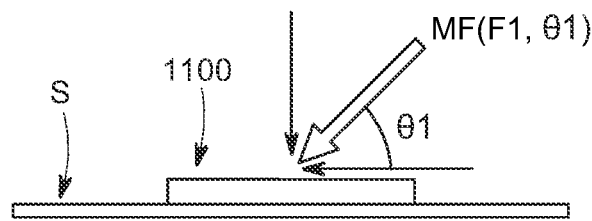
Figure 28B:
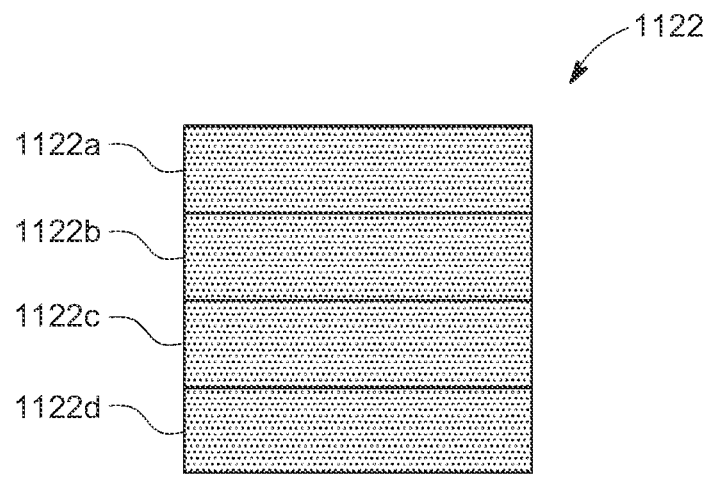
Figure 28C:
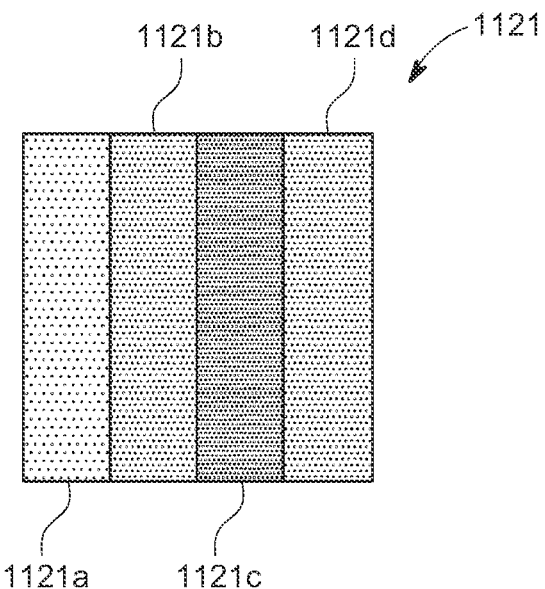

As illustrated in FIGS. 28A-28C, in a case where the multi-directional force (MF) having a first magnitude (F1) greater than the second magnitude (F2) (F1>F2) is applied in the first direction ($\theta 1$), resistance changes of the second unit channels 1122a to 1122d arranged in parallel to the first direction ($\theta 1$) based on the shear axis are the same, a resistance signal of each of the second unit channels 1122a to 1122d has a higher intensity than that sensed in FIG. 27, a change of a resistance signal of the first unit channel 1121c that is almost perpendicular to the first direction ($\theta 1$) is largest among the first unit channels 1121a to 1121d arranged at the predetermined angle with respect to the first direction (θ1) based on the shear axis, and a resistance signal of each of the first unit channels 1121a to 1121d has a higher intensity that that sensed in FIGS. 27A-27C.

Figure 29A:
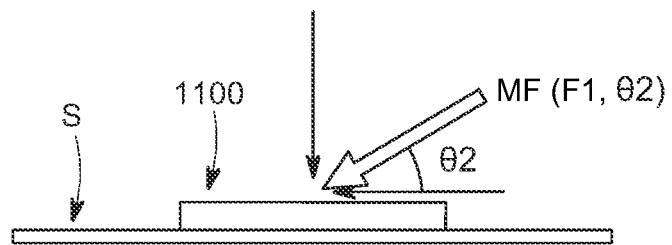
Figure 29B:
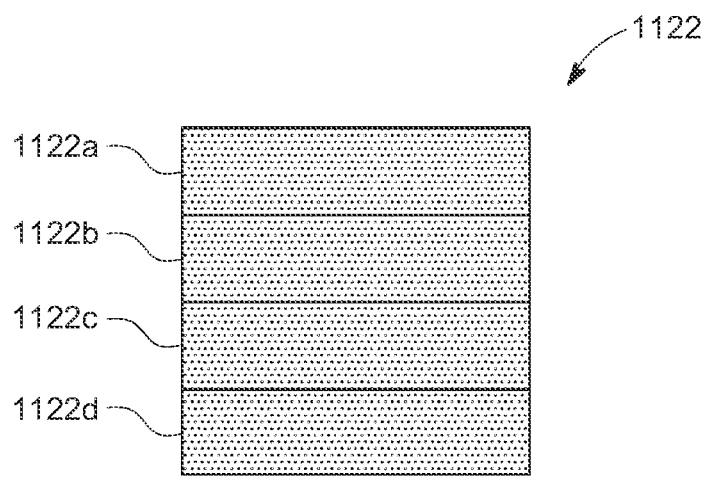
Figure 29C:
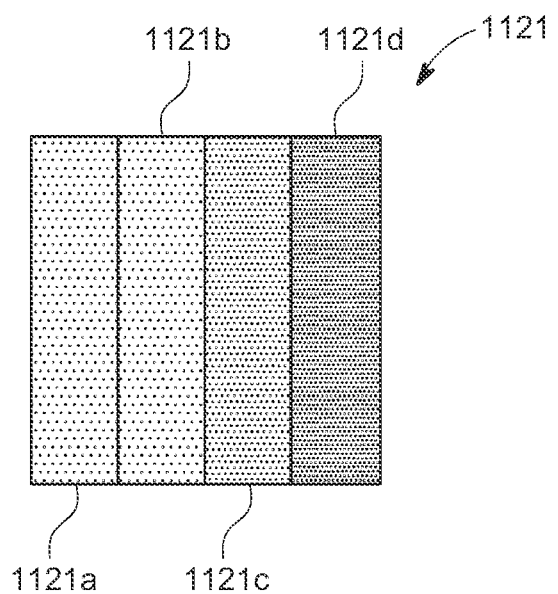

Further, as illustrated in FIGS. 29A-29C, in a case where the multi-directional force (MF) having the first magnitude (F1>F2) is applied in a second direction (θ2) with an angle smaller than that of the first direction (θ1) (θ2<θ1), resistance changes of the second unit channels 1122a to 1122d arranged in parallel to the first direction (θ1) based on the shear axis are the same, a resistance signal of each of the second unit channels 1122a to 1122d has a higher intensity than that sensed in FIG. 27, a change of a resistance signal of the first unit channel 1121d that is almost perpendicular to the first direction (θ1) is largest among the first unit channels 1121a to 1121d arranged at a predetermined angle with respect to the second direction (θ2) based on the shear axis, and a resistance signal of each of the first unit channels 1121a to 1121d has a higher intensity that that sensed in FIG. 27.

Therefore, according to the present invention, it is possible to accurately sense multi-directional force (MF) with different magnitudes applied in different directions.

[6] Method for Manufacturing Multi-Directional Physical Sensor According to Present Invention Hereinafter, a method for manufacturing the multi-directional physical sensor 1100 according to an embodiment of the present invention having the configuration as described above will be described in detail with reference to the drawings.

FIGS. 30A to 30F are process diagrams illustrating a process of manufacturing the first channel 1121 and the bump 1150 of the multi-directional physical sensor 1100 according to an embodiment of the present invention.

Figure 30A:
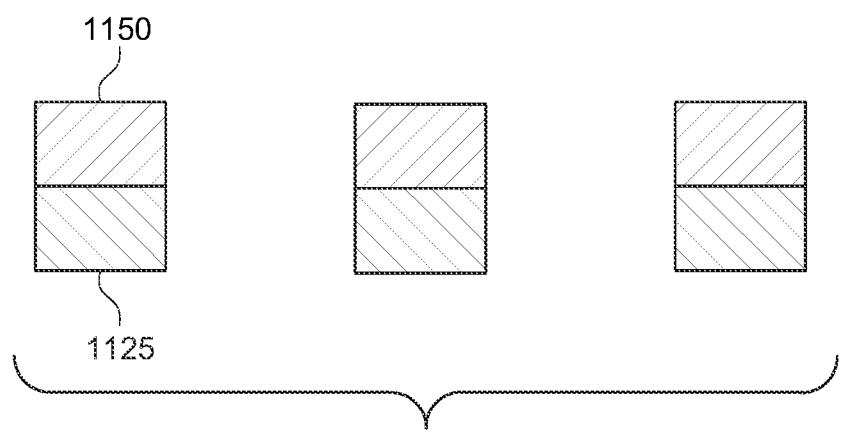
FIGS. 30A to 31D are process diagrams illustrating a method for manufacturing the multi-layer microchannel array according to an embodiment of the present invention.

First, as illustrated in FIG. 30A, a first step (S01) of arranging a plurality of water-soluble molds 1125 having the same shape as the first channel 1121 (see FIG. 26) so as to be spaced apart from each other, and disposing or coupling the bump 1150 on or to the upper side of the water-soluble mold 1125 is performed.

Figure 30B:
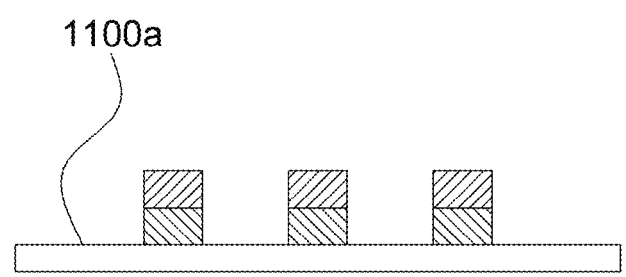

Next, as illustrated in FIG. 30B, a second step (S02) of disposing the water-soluble mold 1125, on which the bump 1150 is disposed, on a base flexible body 1110a is performed. The base flexible body 1110a may be a hardened elastomer.

Figure 30C:
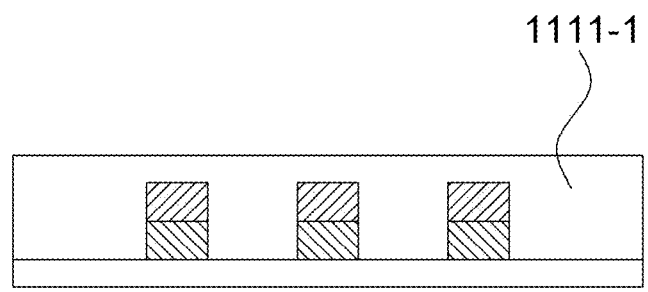

Next, as illustrated in FIG. 30C, a third step (S03) of forming a 1-1-st body 1111-1 by filling a liquid elastomer on the base flexible body 1110a to embed the water-soluble mold 1125 on which the bump 1150 is disposed and then hardening the liquid elastomer is performed. With such a process, an upper portion of the first body 1111a (see FIG. 26) may be formed.

Figure 30D:
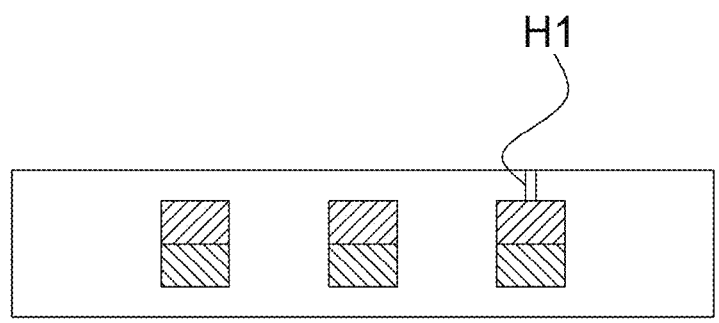

Next, as illustrated in FIG. 30D, a fourth step (S04) of forming a first injection hole H1 in the 1-1-st body 1111-1 so that the water-soluble mold 1125 is in communication with the outside is performed.

Figure 30E:
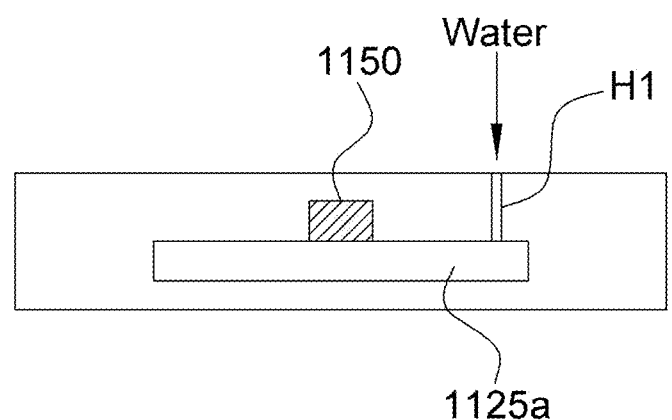

Next, as illustrated in FIG. 30E, a fifth step (S05) of forming a first channel space 1125a by injecting water into the first injection hole H1 to dissolve the water-soluble mold 1125 is performed (FIG. 30E is a cross-sectional view taken along a side surface direction of FIG. 30D).

Figure 30F:
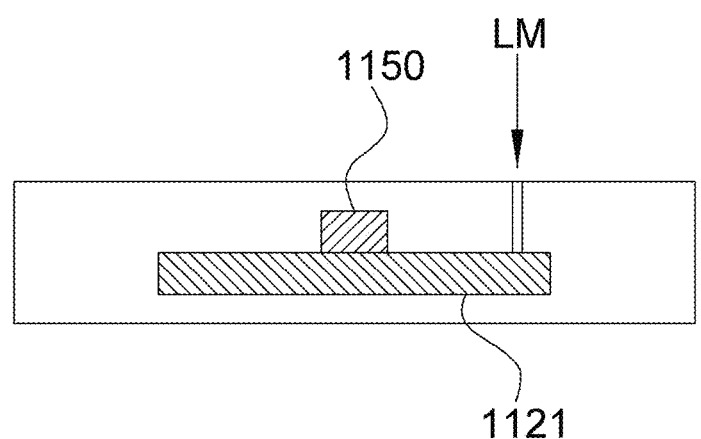

Next, as illustrated in FIG. 30F, a sixth step (S06) of completing the first channel 1121 by injecting a first channel material LM into the first injection hole H1 and hardening the first channel material LM is performed. As the first channel material LM, a liquid metal, for example, galinstan, may be used (FIG. 30F is a cross-sectional view taken along the side surface direction of FIG. 30D).

With such a process, the first channel 1121, the bump 1150, and the 1-1-st body 1111-1 are completed.

FIGS. 31A to 31D are process diagrams illustrating a process in which the second channel 1122 of the multi-directional physical sensor 1100 according to an embodiment of the present invention is manufactured and stacked on the first channel 1121.

Figure 31A:
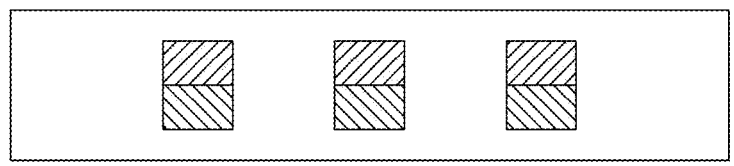

First, as illustrated in FIG. 31A, a seventh step (S07) of disposing the 1-1-st body 1111-1 in which the first channel 1121 and the bump 1150 are embedded is performed.

Figure 31B:
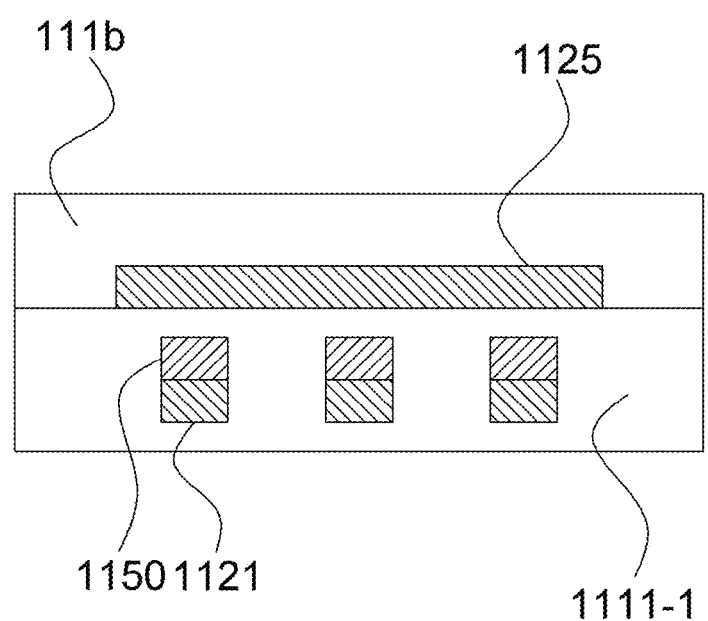
Figure 31C:
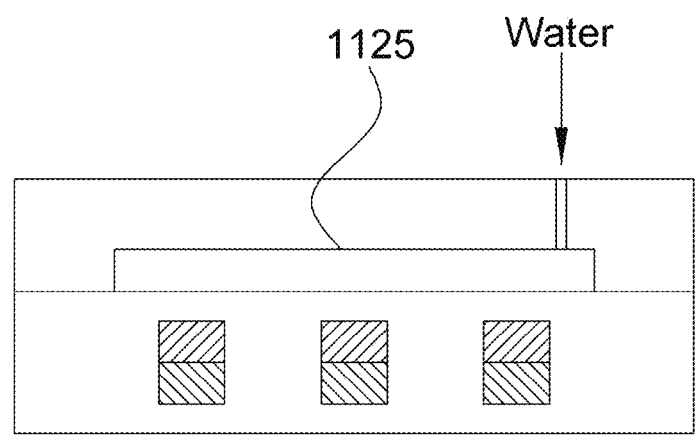
Figure 31D:
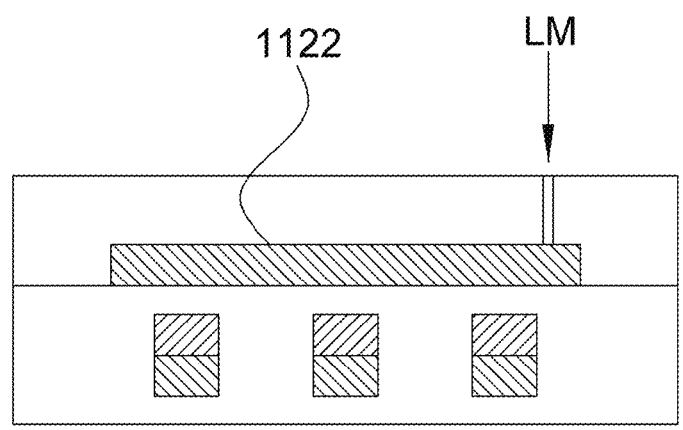

Next, as illustrated in FIG. 31B, an eighth step (S08) of forming a second body 1111b by disposing a water-soluble mold 1125 corresponding to the second channel 1122 (see FIG. 26) on the 1-1-st body 1111-1, and filling and hardening a liquid elastomer is performed.

Next, a ninth step (S09) of forming a second injection hole H2 in the second body 1111b so that the water-soluble mold 1125 is in communication with the outside is performed.

Next, a tenth step (S10) of forming a second channel space 1125b by injecting water into the second injection hole H2 to dissolve the water-soluble mold 1125 is performed.

Next, an eleventh step (S11) of completing the second channel 1122 by injecting a second channel material LM into the second injection hole H2 and hardening the second channel material LM is performed. As the second channel material LM, a liquid metal, for example, galinstan, may be used With such a process, the second channel 1122 and the second body 1111b are completed.

FIGS. 32A to 32D are process diagrams illustrating a process of manufacturing a 1-2-nd body 1111-2 of the multi-directional physical sensor 1100 according to an embodiment of the present invention, the 1-2-nd body 1111-2 being a lower portion of the first body 1111a.

Figure 32A:
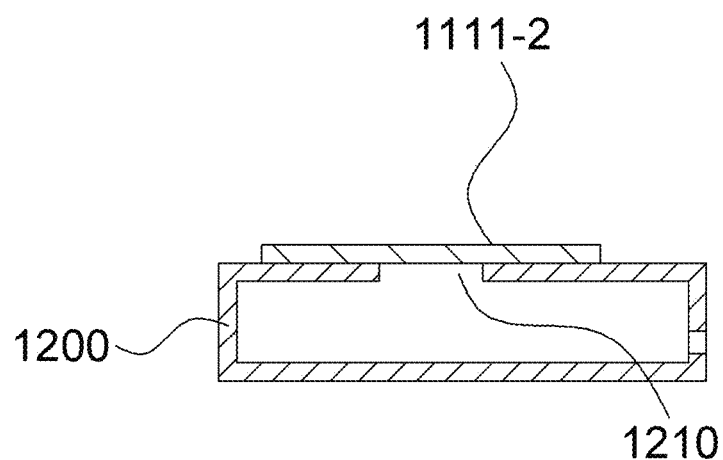
FIGS. 32A to 32D are process diagrams illustrating a method for manufacturing a body having a three-dimensionally protruding shape according to an embodiment of the present invention.
Figure 32B:
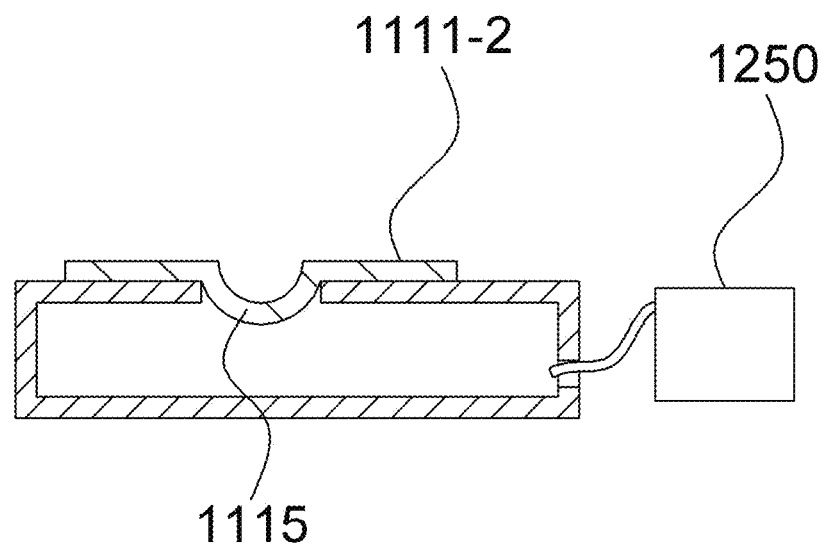
Figure 32C:
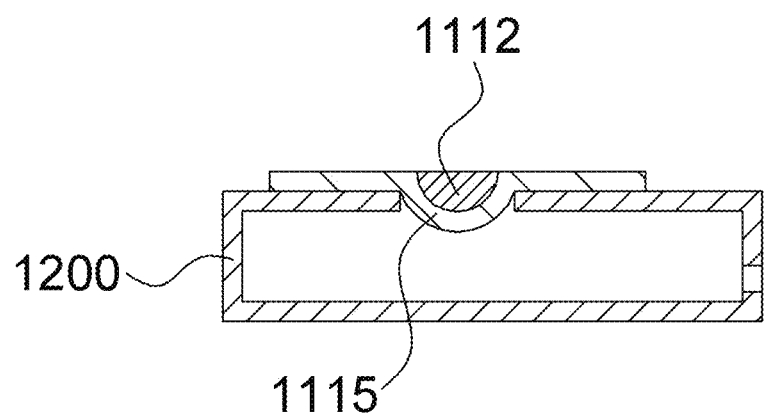
Figure 32D:
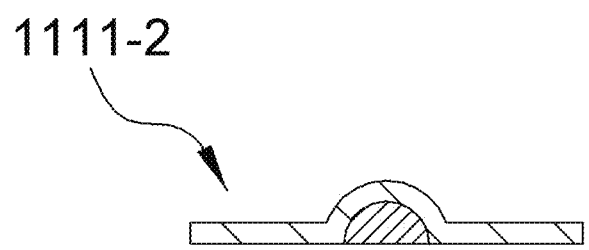

As illustrated in FIG. 32A, a twelfth step (S12) of disposing the 1-2-nd body 1111-2 having a flat plate shape on a chamber 1200 is performed, the chamber 1200 being hollow and having a convex portion forming hole 1210 formed in an upper portion of the chamber 1200. Here, the 1-2-nd body 1111-2 is disposed so that the center of the 1-2-nd body 1111-2 is aligned with the center of the convex portion forming hole 1210.

Next, a thirteenth step (S13) of forming a dome-shaped convex portion 1115 in the 1-2-nd body 1111-2 by forming a negative pressure in the chamber 1200 with a vacuum pump 1250 is performed.

Next, a fourteenth step (S14) of filling a concave portion formed at an upper side of the convex portion 1115 of the 1-2-nd body 1111-2 with the filling material 1112 and hardening the filling material 1112 is performed. The filling material 1112 may be formed of the same elastomer as that of the 1-2-nd body 1111-2, or may be formed of a material with a hardness higher or lower than that of the 1-2-nd body 1111-2.

Next, a fifteenth step (S15) of separating the 1-2-nd body 1111-2 filled with the filling material 1112 from the chamber 1200 and coupling the microchannel 1120 to the upper side of the 1-2-nd body 1111-2 is performed (see FIG. 25).

According to the present invention, as the flexible pressure sensor includes the conductive liquid that has a high conductivity and is highly adaptive to various physical deformations, the elastomer that has a high viscoelasticity, and the microbumps, it is possible to greatly improve flexibility, sensitivity, and stability as compared to the related art. More specifically, since the flexible pressure sensor according to the related art is formed by simply injecting the conductive liquid into the microchannel formed in the elastomer, it is not possible to obtain a sufficient sensitivity. However, according to the present invention, the microbump is added on the microchannel, an external pressure is not dispersed due to the microbump, and may be completely used to cause drastic deformation of the microchannel. Therefore, it is possible to drastically improve the sensitivity several times as compared to the related art.

Further, according to the present invention, the flexible pressure sensor is manufactured by using the microchannel mold that is multi-material 3D-printed by using the sacrificial material and the hard material. As the microchannel mold is manufactured by using 3D printing, the manufacturing may be performed with low costs, in comparison to using the lithography method as in the related art. Further, by adopting the method of using a mold, it is possible to fundamentally prevent a problem of the related art that the thickness of the microchannel may not be adjusted as desired, and it is possible to manufacture the sensor with desired dimensions. In addition, by using the manufacturing method using a multi-material as described above, it is possible to easily insert the microbump for improving the sensitivity into the flexible pressure sensor, and it is also possible to manufacture various multi-dimensional microchannels with various shapes through 3D patterning.

As such, according to the present invention, it is possible to manufacture, in a much easier manner with a high degree of freedom, the flexible pressure sensor with greatly improved flexibility, sensitivity, and stability in comparison to the related art. Therefore, it is possible to improve performance of a wearable device in which the flexible pressure sensor is used, and greatly improve utilization efficiency.

Meanwhile, with the multi-directional physical sensor using the multi-layer microchannel array according to the present invention having the configuration as described above, and a method for manufacturing the same, a normal force, a shear force, or a multi-directional force applied in a three-dimensional direction may be sensed, the multi-directional force being a combination of the normal force and the shear force, and thus it is possible to accurately measure a magnitude and direction of the multi-directional force.

Further, according to the present invention, a force is sensed through a resistance change of the multi-layer microchannel array formed of a liquid metal and thus the signal is not influenced by an external conductor, such that it is possible to accurately measure a magnitude and direction of a multi-directional force applied to the sensor.

Further, according to the present invention, the multi-layer microchannel array is provided on an outer side of the body having a three-dimensionally protruding shape and is disposed adjacent to a portion where an external force is applied, such that sensitivity is improved.

Therefore, according to the present invention, it is possible to manufacture a flexible physical sensor with excellent elasticity, stability, and sensitivity. As a result, various wearable devices for health monitoring may be manufactured. In particular, such a wearable device may surround the skin without causing discomfort in motion and may continuously measure vital signs and body pressure distribution even in a state in which the user does not recognize the measurement.

The present invention is not limited to the abovementioned exemplary embodiments, but may be variously applied. In addition, the present invention may be variously modified by those skilled in the art to which the present invention pertains without departing from the gist of the present invention claimed in the claims.

What is claimed is:

1. A flexible pressure sensor comprising:
   a flexible body formed of an elastomer and in which a microchannel is formed;
   a conductive material formed of a conductive liquid and filling the microchannel; and
   a plurality of microbumps formed of a hard material and disposed to be in surface-contact with an upper surface or a lower surface of a part of the microchannel,
   wherein the microchannel includes: a first channel including a plurality of first unit channels having a predetermined length and arranged while being spaced apart from each other at a predetermined interval along a plane; and
   a second channel disposed on an upper side of the first channel and including a plurality of second unit channels having a predetermined length and arranged while being spaced apart from each other at a predetermined interval along the plane, the second unit channels intersecting with the first unit channels at a predetermined angle along the plane.

2. The flexible pressure sensor of claim 1, wherein the microbumps are formed on the sensing portion of the microchannel.

3. The flexible pressure sensor of claim 1, wherein the sensing portion of the microchannel is formed in a meandering channel shape.

4. The flexible pressure sensor of claim 1, wherein when a direction in which the microchannel extends is an extending direction, a direction parallel to a thickness of the flexible pressure sensor is a thickness direction, and a direction perpendicular to the extending direction and the thickness direction and parallel to a width of the microchannel is a width direction, a width or thickness of the reservoir is larger than a width or thickness of the sensing portion.

5. The flexible pressure sensor of claim 1, wherein when a direction in which the microchannel extends is an extending direction, a direction parallel to a thickness of the flexible pressure sensor is a thickness direction, and a direction perpendicular to the extending direction and the thickness direction and parallel to a width of the microchannel is a width direction, sensitivity of the flexible pressure sensor is adjusted by adjusting a ratio ($k_t=t/z$) of a thickness (t) of the microbump to a thickness (z) between a surface of the flexible pressure sensor that faces the microbump, and a surface of the microchannel that faces the microbump, or by adjusting a ratio ($k_w=d/w$) of a width (d) of the microbump to the width (w) of the microchannel.

6. The flexible pressure sensor of claim 5, wherein the flexible pressure sensor has an embedded bump structure in which $k_t<1$ and $k_w<1$, an exposed bump structure in which $k_t\geq1$, or an anchored bump structure in which $k_w\geq1$.

7. The flexible pressure sensor of claim 6, wherein the microchannel forms a single route or multiple routes, and includes a sensing portion integrated in a predetermined shape at a predetermined position in the flexible body, a reservoir disposed to be spaced apart from the sensing portion, positioned at a distal end of the route, having a cross-sectional area larger than that of the sensing portion, and to which a signal line for transmitting and receiving a signal to and from the outside is connected, and a connection portion connecting the sensing portion and the reservoir, and
   the microbump having the anchored bump structure is formed in the connection portion.

8. The flexible pressure sensor of claim 5, wherein as $k_t$ is increased, the sensitivity of the flexible pressure sensor is increased.

9. The flexible pressure sensor of claim 5, wherein in a case in which $0<k_w<1$, as $k_w$ is increased, the sensitivity of the flexible pressure sensor is increased, and
in a case in which $k_w \geq 1$, as $k_w$ is increased, the sensitivity of the flexible pressure sensor is decreased.

10. A method for manufacturing the flexible pressure sensor of claim 1, the method comprising:
a mold printing step of performing three-dimensional (3D)-printing of a micromold having a 3D shape corresponding to a shape of the microchannel by using a sacrificial material;
a bump printing step of performing 3D-printing of the microbump at a predetermined position on an upper surface of the micromold by using a hard material;
a primary body forming step of primarily coating a flexible material that is a material of the flexible body on a substrate to form a flexible material layer;
a mold disposing step of disposing a coupled body of the micromold and the microbump on an upper surface of the flexible material layer;
a secondary body forming step of secondarily coating the flexible material on the flexible material layer and an upper surface of the coupled body and hardening the flexible material to form the flexible body in which the coupled body is embedded;
a channel forming step of forming the microchannel in the flexible body by removing the micromold; and
a manufacturing completion step of filling the microchannel with the conductive material to complete manufacturing of the flexible pressure sensor.

11. A pulse measurement system comprising:
the flexible pressure sensor of claim 1 that is attached to a wrist of a user and measures a pulse; and
three electrodes that are attached to a body of the user, measure an electrocardiogram (ECG), and include Ref, In+, and In−.

12. The pulse measurement system of claim 11, wherein the pulse measurement system calculates a blood pressure of the user by using a pulse transit time which is a difference between a pulse peak point and an electrocardiogram peak point.

13. A body pressure distribution measurement system comprising:
a plurality of flexible pressure sensors of claim 1 that are distributed on clothes of a user and perform pressure measurement; and
a monitoring unit that performs real-time monitoring of a pressure applied to a body of the user by using a pressure measured by the plurality of flexible pressure sensors.

14. The body pressure distribution measurement system of claim 13, wherein the flexible pressure sensors are distributed at positions corresponding to bony areas including shoulders, wing bones, elbows, knees, and a tailbone which are body parts that are likely to get a bedsore.

15. A blood pressure estimation system comprising:
the flexible pressure sensor of claim 1 that is attached to a wrist of a user and measures a pulse; and
three electrodes that are attached to a body of the user, measure an electrocardiogram (ECG), and include Ref, In+, and In−,
wherein a blood pressure of the user is estimated by using a pulse transit time (PTT) which is a difference between a pulse peak point measured using the flexible pressure sensor and an electrocardiogram peak point measured using the three electrodes.

16. A flexible pressure sensor, comprising:
a flexible body formed of an elastomer and in which a microchannel is formed; and a conductive material formed of a conductive liquid and filling the microchannel,
wherein the flexible body includes a protruding portion that protrudes outward,
the microchannel is disposed adjacent to an upper side of the flexible body along the protruding portion in order to have a curvature, and
the microchannel includes: a first channel including a plurality of first unit channels having a predetermined length and arranged while being spaced apart from each other at a predetermined interval along a plane; and
a second channel disposed on an upper side of the first channel and including a plurality of second unit channels having a predetermined length and arranged while being spaced apart from each other at a predetermined interval along the plane, the second unit channels intersecting with the first unit channels at a predetermined angle along the plane.

17. A flexible pressure sensor of claim 16, comprising:
a flexible body formed of an elastomer and in which a microchannel is formed; and a conductive material formed of a conductive liquid and filling the microchannel,
wherein the flexible body includes a protruding portion that protrudes outward,
the microchannel is disposed adjacent to an upper side of the flexible body along the protruding portion in order to have a curvature, and includes a plurality of unit channels having a predetermined length and arranged while being spaced apart from each other at a predetermined interval along a plane, and
the unit channel is bent along the plane so that opposite ends face different directions, respectively.

* * * * *